(12) United States Patent
Etter et al.

(10) Patent No.: US 12,245,587 B2
(45) Date of Patent: Mar. 11, 2025

(54) POLLEN PRESERVATION METHOD

(71) Applicant: Accelerated Ag Technologies, LLC, Ankeny, IA (US)

(72) Inventors: Sara Katherine Etter, Mitchellville, IA (US); Federico Valverde, Polk City, IA (US); Jason Cope, Ankeny, IA (US); Todd Krone, Johnston, IA (US)

( * ) Notice: Subject to any disclaimer, the term of this patent is extended or adjusted under 35 U.S.C. 154(b) by 293 days.

(21) Appl. No.: 16/028,626

(22) Filed: Jul. 6, 2018

(65) Prior Publication Data

US 2019/0008144 A1    Jan. 10, 2019

Related U.S. Application Data

(60) Provisional application No. 62/529,198, filed on Jul. 6, 2017.

(51) Int. Cl.
| | | |
|---|---|---|
| *A01G 7/00* | (2006.01) | |
| *A01H 1/02* | (2006.01) | |
| *A01N 3/00* | (2006.01) | |

(52) U.S. Cl.
CPC ........... *A01N 3/00* (2013.01); *A01G 7/00* (2013.01); *A01H 1/02* (2013.01)

(58) Field of Classification Search
CPC .................................. A01G 7/00; A01H 1/02
USPC ............................................. 47/1.41, 58.1 R
See application file for complete search history.

(56) References Cited

U.S. PATENT DOCUMENTS

| | | | |
|---|---|---|---|
| 2,669,066 A | 2/1954 | Antles | |
| 4,087,937 A | 5/1978 | Meador | |
| 5,596,838 A | 1/1997 | Greaves et al. | |
| 5,689,914 A | 11/1997 | Greaves et al. | |
| 5,694,700 A | 12/1997 | Greaves et al. | |
| 6,141,904 A | 11/2000 | Greaves et al. | |
| 6,146,884 A * | 11/2000 | Coonrod | G01N 1/42 34/402 |
| 6,865,556 B2 | 3/2005 | Penner et al. | |
| 8,158,850 B2 | 4/2012 | Feng et al. | |

(Continued)

FOREIGN PATENT DOCUMENTS

| | | |
|---|---|---|
| CA | 966734 | 4/1975 |
| CN | 1118650 | 3/1996 |

(Continued)

OTHER PUBLICATIONS

Swift, J.G.; Buttrose, M.S. (1972). Freeze-etch studies of protein bodies in wheat scutellum. J. Ultrastruct. Res. 40:378-390.

(Continued)

*Primary Examiner* — David J Parsley
(74) *Attorney, Agent, or Firm* — Brick Gentry PC; Brian J. Laurenzo; Charles M. Forney

(57) ABSTRACT

Disclosed are methods of preserving pollen such that the pollen has improved viability as compared to pollen that is left in ambient conditions. A method of the present invention includes separating dead pollen contents from live pollen grains. In some embodiments, pollen grains are stored with a substance that prevents dead pollen contents from interacting with live pollen grains. The substance may be a solid, liquid, gas, or combination thereof. In some embodiments, the substance may at least partially regulate pollen moisture content, such as maintaining pollen moisture content at 15-60%.

17 Claims, 17 Drawing Sheets

(56) References Cited

U.S. PATENT DOCUMENTS

| | | | |
|---|---|---|---|
| 8,356,464 B2 | 1/2013 | Lafargue et al. | |
| 8,618,358 B2 | 12/2013 | Feng et al. | |
| 8,943,745 B2 | 2/2015 | Sexton et al. | |
| 9,227,230 B2 | 1/2016 | Bensley-Bromilow et al. | |
| 9,433,161 B2 | 9/2016 | Cope et al. | |
| 2013/0118066 A1 | 5/2013 | Cope et al. | |
| 2013/0118067 A1 | 5/2013 | Cope et al. | |
| 2014/0115730 A1* | 4/2014 | Cope | A01H 1/02 800/260 |
| 2014/0208648 A1* | 7/2014 | Cox | A01C 1/04 47/65.5 |
| 2014/0223812 A1 | 8/2014 | Cope et al. | |
| 2014/0271535 A1* | 9/2014 | Yamashita | A01N 25/12 424/84 |
| 2015/0253273 A1* | 9/2015 | Heidmann | G01N 27/20 435/29 |

FOREIGN PATENT DOCUMENTS

| | | | |
|---|---|---|---|
| CN | 1762202 | | 4/2006 |
| CN | 104145947 | | 10/2014 |
| CN | 104498426 | | 4/2015 |
| CN | 104957032 | | 10/2015 |
| CN | 105104363 | | 12/2015 |
| CN | 105191581 | | 12/2015 |
| CN | 106242627 | | 12/2016 |
| CN | 205926293 | | 2/2017 |
| CN | 107494522 | | 12/2017 |
| JP | 6-157201 | * | 6/1994 |
| JP | H11192033 | | 7/1999 |
| JP | 2004-357628 | * | 12/2004 |
| JP | 200904703 | | 2/2009 |
| JP | 2009040703 | | 2/2009 |
| JP | 2009178083 | | 8/2009 |
| SU | 1061770 | | 12/1983 |
| SU | 1340668 | * | 9/1987 |
| SU | 1606037 | | 11/1990 |
| WO | 2012125593 | | 9/2012 |
| WO | 2013070846 | | 5/2013 |
| WO | 2014209903 | | 12/2014 |
| WO | 2016085355 | | 6/2016 |
| WO | 2017180849 | | 10/2017 |
| WO | 2018129302 | | 7/2018 |

OTHER PUBLICATIONS

Virmani, S.S. and M. Llyas Ahmed. (2001). Environment-sensitive genic male sterility (EGMS) in crops. Adv. Agronomy 72: 139-195. DOI: 10.1016/S0065-2113(01)72013-5.
Walden, D. B. (1967). Male Gametophyte of *Zea mays* L. Crop Science 7:441-443.
Wang, Z; Ge, Y.; Scott, M and Spangenberg, G. (2004). Viability and longevity of pollen from transgenic and non-transgenic tall Fescue (*Festuca arundinacea*) (*Poaceae*) Plants. American Journal of Botany 91(4): 523-530.
Webb, M.A.; Arnott, H.J. (1982). Cell wall conformation in dry seeds in relation to the preservation of structural integrity during desiccation. Am. J. Bot. 69:1657-1668.
Pareddy et al. (1989). Production of normal, germinable and viable pollen from in vitro-cultrued maize tassels. Theor Appl. Genet. 77:521-526.
Aylor, Donald E. (2004). Survival of maize (*Zea mays*) pollen exposed in the atmosphere. Agricultural and Forest Meteorology 123 (2004) 125-133.
Buitink et al. (2000). The effects of moisture and temperature on the ageing kinetics of pollen: interpretation based on cytoplasmic mobility. Plant Cell and Environment (2000) 23, 967-974.
Everett, H.L. (? 1950s?) Studies on Com Pollen. Thirteenth Hybrid Corn Industry Research Conference.
Kerhoas C. et al. (1987). A multidisciplinary approach to the study of the plasma membrane of *Zea mays* pollen during controlled dehydration. Plana 171: 1-10.

Nath, J. et al. (1975) Effect of Freezing and Freeze-Drying on the Viability and Storage of *Lilium longiflorum* L. and *Zea mays* L. Pollen. Cryobiology 12, 81-88.
Nepi, M. et al. (2001). Pollen hydration status at dispersal: cytophysiological features and strategies. Protoplasma (2001) 216: 171-180.
International Search Report and Written Opinion of the International Searching Authority regarding PCT/US2016/039339 filed on Jun. 24, 2016.
Synchronous Pollination within and between Ears Improves Kernel Set in Maize, Crop Science, vol. 40, No. 4, Jul. 2000, pp. 1056-1061.
International Search Report and Written Opinion of the International Search Authority regarding PCT/US2016/039355 filed on Jun. 24, 2016.
R T Weiland: Cross-Pollination Effects on Maize (*Zea mays* L.) hybrid yields, Can, J. Plant Sci, vol. 72, No. 1, Jan. 1, 1992, pp. 27-33.
Cherng-Liang Tsai Et Al: Effects of cross-pollination on dry matter accumulation, nutrient partitioning and grain yield of maize hybrids grown under different levels of N fertility, Journal of the Science of Food and Agriculture, vol. 57, No. 2, Jan. 1, 1991, pp. 163-174.
J M Shete et al: Study of Heterosis in Top Cross Derivatives of Maize (*Zea mays* L.), Agric. Sci. Digest, vol. 31, No. 1, Mar. 1, 2011, pp. 1-7.
Want R F et al: Leaf photosynthesis is enhanced in normal oil maize pollinated by high oil maize hybrids, Industrial Crops and Products, Elsevier, NL, vol. 29, No. 1, Jan. 1, 2009, pp. 182-188.
Uribelarrea et al: Enhanced kernel set promoted by synchronous pollination determines a tradeoff between kernel number and kernel weight in temperate maize hybrids, Field Crops Research, Elsevier, Amsterdam, Nl, vol. 105, No. 3, Nov. 19, 2007, pp. 172-181.
Carcova Jorgelina et al: Synchronous pollination within and between ears improves kernel set in maize, Crop Science, vol. 40, No. 4, Jul. 2000, pp. 1056-1061.
Sanford, J.C. and R. E. Hanneman, Jr., The Common Potato Pollen Collector Modified for Bulk Pollen Collection, 1977, News and Reviews.
Bhargava, et al., 1991, An Efficient Potato Pollen Extractor for Bulk Pollen Collection.
Office Action dated Jun. 19, 2018 from U.S. Appl. No. 15/192,519 Covering Grain Production.
Tsai et al, Journal of the Science of Food and Agriculture 57: 163-174, Effects of Cross-pollination on Dry Matter Accumulation, Nutrient Partitioning and Grain Yield of Maize Hybrids Grown under Different Levels of N Fertility.
Wang et al, 2009, Industrial Crops and Products 29: 182-188, Leaf Photosynthesis is enhanced in normal oil maize pollinated by high oil maize hybrids.
Graybosch et al, 1988, American Journal of Botany 75: 144-156, Male Sterility in soybean—An Overview.
Ortiz-Perez et al, 2007, Field Crops Research 101: 259-268, Insect-mediated cross-pollination in soybean.
United States Office Action U.S. Appl. No. 15/192,485 Covering Seed Production dated Jan. 22, 2018.
International Search Report and Written Opinion of the International Searching Authority from PCT/US2017/027381.
Cicero Almeida et al: Conservation and in vitro germination of pollen of maize, Brazilian Journal of Botany, vol. 34, Oct. 1, 2011, pp. 493-497.
Connor Kristina F Et Al: Pollen-handling protocol and hydration/dehydration characteristics of pollen for application to long-term storage, Euphytica, vol. 68, No. 1-2, 1993, pp. 77-84.
Forsberg R A et al: Sources, Maintenance, and Utilization of Parental Material, Jan. 1, 1980 (Jan. 1, 1980), hybridization of crop plants, American Society of Agronomy, Inc.: Crop Science Society of America, Madison, WI, pp. 65-81.
N. Sukhvibul et al: Medium and long term storage of Anigozanthos manglesii (D. Don) pollen, New Zealand Journal of Crop and Horticultural Science, vol. 21, No. 4, Dec. 1, 1993 (Dec. 1, 1993), pp. 343-347.
Barnabas B et al: Adhesion and Germination of Differently Treated Maize Pollen Grains on the Stigma, ACTA Botanica Hungarica, vol. 30, No. 3-4, 1984, pp. 329-332.

(56) References Cited

OTHER PUBLICATIONS

Urs Weingartner, Olivier Kaeser, Muhua Long, and Peter Stamp: Combining Cytoplasmic Male Sterility and Zenia Increases Grain Yield of Maize Hybrids, Crop Science, pp. 1848-1856 (2002).
Office Action dated Oct. 12, 2018 from U.S. Appl. No. 15/192,485 Covering Seed Production.
Communication pursuant to Article 94(3) EPC regarding European Patent Application No. 16 739 302.4 dated Feb. 12, 2019 Covering Seed Production.
Communication pursuant to Article 94(3) EPC regarding European Patent Application No. 16 738 296.9 dated Feb. 18, 2019 Covering Grain Production.
Communication pursuant to Rules 161(1) and 162 EPC regarding European Patent Application No. 17 718 712.7 dated Feb. 12, 2019 Covering Pollen Field Conditioning and Preservation Method.
Koga, Y., et al. (1971). Studies on the longevity of pollen grains of rice, Oriza sativa L. 1. Morphological change of pollen grains after shedding. Cytologia 36: 104-110.
Mouradian, R.; Womersley, C.; Crowe, L.M.; Crowe, J.H. (1985). Degradation of functional integrity during long-term storage of a freeze-dried biological membrane. Cryobiology 22:119-127.
Nirmala, B., et al. (2009). Economics of hybrid rice seed production in India. p. 495-503. In: F. Xie and B. Hardy (eds) Accelerating Hybrid Rice Development. Intl Rice Research Institute.
Pfahler, P. L.; Linskens, H. F. (1972). In vitro germination and pollen tube growth of maize (*Zea may* 42:136-140. L.) pollen Theoretical and Applied Genetics.
Platt-Aloia, K.A.; Lord, E.M.; de Mason, D.A.; Thompon, W.W. (1986). Freeze fracture observations on membranes of dry and hydrated pollen from Colomia, Phoenix and Zea. Planta 168:291-298.
Platt-Aloia, K.A.; Thomson, W.W. (1985). Freeze-fracture evidence of gel-phase lipid in membranes of senescing cowpea cotyledons. Planta 163:360-369.
Priestley, D.A.; De Kruijff, B. (1982). Phospholipid motional characteristics in a dry biological system. A 31P nuclear magnetic resonance study of hydrating *Typha latifolia* pollen. Plant Physiol. 70:1075-1078.
Priestley, D.A.; Werner, B.G.; Leopold, A.C.; McBride, M.B. (1985). Organic free radical levels in seeds and pollen: the effects of hydration and aging. Physiol. Plant. 64:88-94.
Senaratna, T.; McKersie, B.D.; Stinson, R.H. (1985). Simulation of dehydration injury to membranes from soybean axes by free radicals. Plant Physiol. 77:472-474.
Song, Z.P., et al. (2001). A study of pollen viability and longevity in Oryza rufipogon, O. sativa, and their hybrids. p. 31-32. IRRI Pub. 26.2.
Southworth, D.; Branton, D. (1971). Freeze-etched pollen walls of Artemisia pycnocephala and Lolium humboldtii. J. Cell Sci. 9:193-207.
Office Action dated Feb. 9, 2018 from U.S. Appl. No. 15/192,519 Covering Grain Production.
Office Action dated Apr. 30, 2018 from U.S. Appl. No. 15/486,737 Covering Pollen Field Conditioning and Preservation Method.
Almeida et al (Brazilian Journal of Botany (2011), Conservacao e germinacao in vitro de polen de milho, vol. 34 (4), pp. 193-497.
Volk, Gayle (2011) Collecting Pollen for Genetic Resources Conservation. Ch. 25.
Connor, Kristina F. (1993) Pollen-Handling protocol and hydration/dehydration characteristics of pollen for application to long-term storage.
Barnabas, B. and Rajki, E. (1976). Storage of Maize (*Zea mays* L.) Pollen at—196° C. in Liquid Nitrogen. Euphytica 25:747-752.
Barnabas, B. (1985). Fertility of deep-frozen maize (*Zea mays* L.) pollen. Ann. Bot. 48:861-864.
Barnabas B. and Rajki, E. (1981). Effect of water loss on germination ability of maize (*Zea mays* L.) pollen. Ann. Bot. 55:201-204.
Barnabas, B; Kovacs, G.; Abranyi, A.; and Pfahler, P. (1988). Effects of Pollen Storage by Drying and Deep-Freezing on the Expression of Different Agronomic Traits in Maize (*Zea mays* L.). Kluwer Academic Publishers, Dordrecht—Printed in the Netherlands. Euphytica 39(3):221-225.
Barnabas, B (1994). Preservation of Maize Pollen Biotechnology in Agriculture and Forestry, vol. 25 Maize (ed. by Y. P. S. Bajaj) Springer-Verlag Berlin Heidelberg.
Barnabas, B., and G. Kovacs. (1997). Storage of Pollen. Ch. 14, In: K.R. Shivanna and V. K. Sawhney (eds). Pollen Biotechnology for Crop Production and Improvement. Cambridge University Press.
Basra, A. (1999). Heterosis and Hybrid Seed Production in Agronomic Crops, 81-84.
Collins, T. C.; Lertmongkol, V.; Jones, J. P. (1973). Pollen Storage of Certain Agronomic Species in Liquid Air, Crop Science, 13:493-494.
Connor, Kristina and Towill, Leigh. (1993). Pollen-Handling Protocol and Hydration/Dehydration Characteristics of Pollen for Application to Long-Term Storage, KluwerAcademics Publisher 77-84.
Crevecoeur, M; Clegg, J.S.; Seitz, P.; Seitz, W.; Hazlewood, C.F. (1982). Cellular responses to extreme water loss: the water-replacement hypothesis. Cryobiology 19:306-316.
Crevecoeur, M.; Deltour, R.; Bronchart, R. (1982). Quantitative freeze-fracture study of plasmalemma and nuclear envelope of *Zea mays* root cells during early germination. J. Ultrastruct. Res. 80:1-11.
Das, S.; Singhal, G.S. (1985). Role of interfacial structured water in membrane: osmotic properties of L-α-Egg lecithin liposomes. J. Membr. Biol. 86:221-227.
Office Action dated Apr. 12, 2019 from U.S. Appl. No. 15/486,737 Covering Pollen Field Conditioning and Preservation Method.
Ishikawa, M. Kitashima, T., Hemachandra, P.V., Yamaguchi, E. and Toyomasu, T. (2005), Seed Sci. & Technol., 33, 7541-752 Constant relative humidity chgambers using phosphoric acid for controlled desiccation of small recalcitrant.
Notification Concerning Transmittal of International Preliminary Report on Patentability and International Preliminary Report on Patentability from PCT/US2016/039339.
Notification Concerning Transmittal of International Preliminary Report on Patentability and International Preliminary Report on Patentability from PCT/US2016/039355.
Dickinson, H.G.; Elleman, C.J. (1985). Structural changes in the pollen grain of *Brassica oleracea* during dehydration in the anther and development on the stigma as revealed by anhydrous fixation techniques. Micron Micros. Acta 16:255-270.
Elleman, C.J.; Dickinson, H.G. (1986). Pollen stigma interactions in *Brassica*. IV. Structural reorganisation in the pollen grains during hydration. J. Cell Sci. 80:141-157.
Ganeshan, S., et al. (2008). Cryopreservation of Pollen. Ch. 17, In: B.M. Reed (ed), Plant Crypreservation: A Practical Guide. Springer.
Heslop-Harrison, J. (1979). An interpretation of the hydrodynamics of pollen. Amer. J. Bot. 66: 737-743.
Heslop-Harrison, J.; Heslop-Harrison, Y. (1985). Germination of stress tolerant Eucalyptus pollen. J. Cell Sci. 73:135- 157.
Hoekstra, F.A., and J. Bruinsma. (1975). Respiration and vitality of binucleate and trinucleate pollen. Physiol. Plant. 34: 221-225.
Kaku, S.; Iwayainove, M.; Gusta, L.V. (1984). Relationship of nuclear magnetic resonance relaxation time to water content and cold hardiness in flower buds of evergreen azalea. Plant Cell Physiol. 25:75-882.
Khatum, S., and T.J. Flowers. (1995). The estimation of pollen viability in rice. J. Exp. Bot. 46:151-154.
King, J.R. (1965). The storage of pollen-particularly by the freeze drying method. Bull. Torrey Bot. Soc. 92: 270-287.
Chilean Patent Office, Application No. 20200005 Office Action dated Jul. 12, 2021.
China Intellectual Property, Application No. 2018880045124.8 Office Action dated May 17, 2021.
Indian Patent Office, Application No. 202037003857 Office Action dated Jul. 16, 2021.
Chinese National Intellectual Property Administration Second Office Action dated Dec. 8, 2021, Application No. 201880045124.8.
European Patent Office Office Action dated Oct. 4, 2021, Application No. 18 746 399.7.

(56) References Cited

OTHER PUBLICATIONS

Russian Federal Institute for Industrial Property Office Action dated Dec. 6, 2021, Application No. 2020104987.
Yi, Weiguang et al, Polyester and Nylon Powders Used as Pollen Diluents Preserve Pollen Germination and Tube Growth in Controlled Pollinations, Sexual Plant Reproduction 15 (2003), pp. 265-269, https://doi.org/10.1007/s00497-002-0160-6 (abstract only).
European Patent Office, Communication Pursuant to Article 94(3) EPC, Application No. 18 746 399.7-1110, dated Nov. 10, 2022.
Servico Publico Federal Ministerio Da Economia (Brazil), Preliminary Requirement (no English translation), Application No. BR112020000213-5 dated Jun. 9, 2022.
Presentado Por Sistema De Gestion De Peritos Internet (Chile), Office Action, Application No. 202000005, dated Jul. 1, 2022.
China National Intellectual Property Administration, Text of Rejection Decision, Application No. 201880045124.8 dated Jun. 17, 2022.
European Patent Office Communication Pursuant to Article 94(3) EPC, Application No. 18 746 399.1-1110, dated Apr. 21, 2022.
Russian Federal Service for Intellectual Property, Office Action, Application No. 2020104987, dated Jul. 4, 2022.
Ukraine Patent Office, Application No. 2020 00545, Office Action dated Jun. 30, 2023.
European Patent Office, Communication Pursuant to Rule 115(1) EPC, Application No. 18 746 399.7-1110, dated May 24, 2023.
Canadian Innovation, Science and Economic Development Canada, Application No. 3,068,767, Office Action dated Jul. 25, 2023.

* cited by examiner

Fig. 9

POLLEN PRESERVATION METHOD

This application claims priority from U.S. Provisional Application Ser. No. 62/529,198 filed Jul. 6, 2017 and entitled METHOD OF IMPROVING POLLEN VIABILITY AND STORABILITY. The contents of U.S. Provisional Application Ser. No. 62/529,198 are hereby incorporated in their entireties by reference.

FIELD OF THE INVENTION

This invention relates generally to a novel method for increasing the overall viability and fertility of pollen and preventing pollen necrosis, which results in improved pollen for use in pollinating plants. The invention may be conducted with either fresh pollen or pollen that has previously been stored or preserved.

BACKGROUND

The current invention has application to the field of pollen longevity and viability. Pollen longevity is significantly influenced by environmental conditions, most notably temperature and relative humidity. Pollen, which is naturally shed from the flowers or flowering structures of angiosperms, is subject to rapid loss of viability once it is shed from the plant. Viability can be lost in minutes to hours depending on species and environmental conditions. Exposure to dry air and high temperature is particularly detrimental to pollen viability and longevity once it is shed from the plant. Thus, under natural field conditions, pollen has a limited lifespan during which it remains viable, referred to in this application as the "viability window", as provided herein below. In particular, pollen from the Poaeceae (Gramineae) family of plants, commonly referred to as grasses, is particularly vulnerable and short-lived (Barnabas & Kovacs (1997) In: *Pollen Biotechnology For Crop Production And Improvement*. (1997). Sawhney, V. K., and K. R. Shivanna (eds). Cambridge University Press. pp. 293-314). This family of plants includes many economically important cereal crops, including maize. Methods to improve pollen viability and extend the duration of its viability are of significant value to the agricultural industry.

Specifically, if pollen collected from plants can be stored in a viable state for a period of time, this pollen may be used to pollinate female flowers as desired in a number of advantageous ways. Utilizing stored pollen allows for pollination which is not dependent on active pollen shed, temporal synchrony with pistil (female flower) receptivity, use of male sterility, and/or physical isolation from other pollen sources. Currently, many species rely on self-pollination or cross pollination by neighboring plants to produce fertile seed or grain. Typically, in the agricultural hybrid seed industry, mechanical, physical, and/or genetic interventions are required to ensure female plants are cross pollinated, and not self-pollinated, so that pollen of a specific genetic constitution is employed to produce hybrid seed. Such measures, for example, are used routinely to produce hybrid maize and rice seed. In some crops, however, even these measures are not as effective to ensure cross pollination by a specific desired pollen source. Currently, it is not economical to produce these crops commercially as hybrids. Examples of these crops include, but are not limited to, wheat and soy.

Many attempts have been made to preserve pollen and extend its viability for pollinations beyond the time the pollen would remain viable if left exposed to uncontrolled ambient conditions. Among the grasses, studies with maize are exemplary of the progress made in pollen preservation. Many types of treatments have been tested for maintaining or extending maize pollen viability and/or fertility. Among them, the favorability of treating and/or storing maize pollen at high humidity and/or cold temperature has been reported by many.

Among the earliest accounts of maize pollen preservation (Andronescu, Demetrius I., The physiology of the pollen of *Zea mays* with special regard to vitality. Thesis for degree of Ph. D. University of Illinois. 1915), it was reported that in the absence of controlled environmental storage conditions, pollen died in two to four hours. By raising the relative humidity of the storage environment, the pollen's viability was maintained for 48 hours. Moreover, storage at low temperature (e.g., 8-14° C.) had a stimulative effect upon the viability of the pollen.

Even when relative humidity is not controlled during storage, maize pollen held at low temperature (e.g., 2-7° C. for 3-120 hours) can more than double its in vitro germinability compared to initial, pre-storage vitality or compared to storage at 35° C. (Pfahler, P. L. and Linskens, H. F., (1973) *Planta*, 111(3), pp. 253-259; Frova, C. B. and Feder, W. A., (1979) *Ann Bot*, 43(1), pp. 75-'79). When high humidity (90% RH) and low temperature (4° C.) during storage are combined for pollen treatment, germination of maize pollen on artificial media remains good, to fair, for eight days (Sartoris, G. B., (1942) *Am J Bot*, pp. 395-400). Storage of maize pollen under the same conditions for eight days also allows the pollen to remain fertile, albeit at a reduced level, and capable of forming kernels on ears following pollination (Jones, M. D. and Newell, L. C., (1948) *J Amer Soc Agron* 40:195-204).

Field conditioning maize pollen at high humidity and low temperature commonly help revive pollen of low viability and/or extend its longevity, whereby at least limited seed formation occurs following pollination of ears. But the stimulative effect of low temperature storage on fertility is not always observed (Walden, D. B., (1967) *Crop Science*, 7(5), pp. 441-444) and if the pollen becomes dehydrated to excessive levels, pollen tube formation on artificial media and silks can be markedly reduced (Hoekstra, F A. (1986) In: *Membranes, Metabolism and Dry Organisms*. (Ed., A C Leopold), pp. 102-122, Comstock Publishing Associates, Ithaca, N.Y.; Barnabas, B. and Fridvalszky, L., (1984) *Acta Bot Hung* 30:329-332).

Although high humidity and low temperature slow the temporal decay of viability during storage of Gramineae pollen, optimizing these environmental conditions for preservation only postpones the complete loss of viability and fertility. Methods in addition to regulating humidity and temperature are needed to further enhance the longevity of stored pollen so that it can be used in commercial practice of supplemental pollination for improved seed and grain production. Further, regulating humidity and temperature in large scale applications is technologically challenging and expensive so simpler approaches would make supplemental pollinations much more feasible.

In some cases, it may be desirable to treat pollen so that it is dehydrated to various degrees. Dehydration can be achieved by vacuum drying or exposing pollen to a relative humidity and temperature (i.e., vapor pressure deficit) that causes water to diffuse out of the pollen. Vapor pressure deficits favorable for pollen drying can be produced in a number of ways, such as with desiccants, mechanical equipment designed to control temperature and relative humidity in an enclosed chamber and with saturated salt solutions held in a closed space (Jackson, M. A. and Payne, A. R. (2007) *Biocontrol Sci Techn,* 17(7), pp. 709-719), Greenspan, L., (1977) *J Res Nat Bur Stand,* 81(1), pp. 89-96)

In an effort to dehydrate and preserve sugarcane pollen, the pollen was stored at low temperature under vacuum with a small amount of $CaCl_2$ desiccant present (Sartoris, G. B. (1942) *Am J Bot,* pp. 395-400). The pollen remained dry throughout storage, as desired, but use of low pressure was not as favorable as storage at normal atmospheric pressure. The behavior of corn pollen was very similar to that of sugarcane. More direct attempts at dehydration have incubated pollen in conditions of established or recorded relative humidity and temperature. These examples show that maize pollen can be dehydrated to very low levels (e.g., 7-10% pollen water content) and still possess an ability, albeit reduced, to effect seed formation following pollination of ears (Barnabas, B., et al. (1988) *Euphytica,* 39(3), pp. 221-225; U.S. Pat. No. 5,596,838).

Dehydration of pollen is commonly performed ahead of freezing for storage and preservation at very low temperatures. As practiced with maize, fresh pollen is dehydrated at room temperature in a vacuum chamber, humidity incubator, or simply with air-drying or mild heat (U.S. Pat. No. 5,596,838; Barnabas, B. and Rajki, E. (1981). *Ann Bot,* 48(6), pp. 861-864; Connor, K. F. and Towill, L. E. (1993) *Euphytica,* 68(1), pp. 77-84). Upon thawing after short or long term storage, cryopreserved pollen can be viable and fertile, but fertility is not always exhibited and some members of the Gramineae family, such as maize, sorghum, oat and wheat, can be difficult to cryopreserve (Collins, F. C., et al. (1973) *Crop Sci,* 13(4), pp. 493-494). One explanation offered for this recalcitrance is excess drying or aging of the pollen (Collins, F. C., et al. (1973) *Crop Sci,* 13(4), pp. 493-494). It is evident that pollen quality can be affected by prevailing environmental conditions during floral development, pollen maturation, and anthesis (Shivanna, K. R., et al. (1991) *Theor Appl Genet* 81(1), pp. 38-42; Schoper, J. B., et al. (1987) *Crop Sci,* 27(1), pp. 27-31; Herrero, M. P. and Johnson, R. R. (1980) *Crop Sci,* 20(6), pp. 796-800). Pollen stressed in these ways could exhibit a reduced propensity to withstand the rigors of dehydration and freezing for cryopreservation. A need exists to overcome this problem and make cryopreservation of Gramineae pollen more attainable and routine so this form of pollen preservation can be implemented in a predictable way on a commercial scale.

Desiccation is known to have a direct impact on pollen viability. Barnabas (1985) *Ann Bot* 55:201-204 and Fonseca and Westgate (2005) *Field Crops Research* 94: 114-125 demonstrated that freshly harvested maize pollen could survive a reduction in original water content of approximately 50%, but few pollen grains demonstrated viability or a capacity for normal pollen tube formation with an additional water loss beyond that level. Early work by Barnabas and Rajki ((1976), *Euphytica* 25: 747-752) demonstrated that pollen with reduced water content would retain viability when cryogenically stored at −196° C. Subsequent work (Barnabas & Rajki (1981) *Ann Bot* 48:861-864) demonstrated that such partially-desiccated maize pollen grains stored at −76° C. or −196° C. also could effect fertilization of receptive female flowers. Other methods of storing pollen for varying periods of time are known in the art, including freeze-drying, vacuum-drying, and storage in organic non-polar solvents. Limitations in the scalability of these pollen preservation techniques combined with the complex, non-portable equipment requirements render these techniques impractical for use with large volumes of pollen required for field-scale applications. For example, the ability to create a vacuum chamber large enough for production-level field pollination preservations would have required a much larger vacuum chamber capable of rapidly changing pressure levels. Production-level parent increase fields are typically an acre or more, while hybrid production fields are typically 10 acres or more in size. Such fields require a considerable amount of pollen and thus a large vacuum chamber would be needed. A chamber of these specifications would require the ability to pump down to a pressure of 5 Torr (0.67 kPa) or less, with the added ability to rapidly up cycle and down cycle this level of pressure. As the physical volume of the sample increases, the ability to generate and cycle at 5 Torr (0.67 kPa) efficiently begins to go beyond what mechanical pumps can generate. In addition, storage of pollen in organic solvents creates hazardous chemical requirements.

U.S. Pat. No. 5,596,838 from Greaves, et al., discloses a method of storing pollen that involves a reduction in moisture level by exposing pollen to reduced atmospheric pressures prior to storage. This technique prepared small quantities of pollen, such as from a single maize plant, for subsequent storage under sub-zero conditions. The methodology and mechanical system requirements, however, lacked the capacity to produce stored pollen in quantities large enough to enable commercial seed production or grain production applications. These requirements effectively negated any opportunity to advance the technology beyond research level investigations. Another Greaves et al. patent, U.S. Pat. No. 6,141,904 provides that pollen may be placed in a carrier material to increase flowability, such as a flowable powder. In addition, U.S. Pat. No. 2,669,066 suggests mixing pollen with substances having a high protein content for treatment and application, such as powdered egg albumin, powdered casein, or powdered milk in instances of short-term storage.

The availability of preserved, viable pollen overcomes many of the production challenges faced by the hybrid seed industry. With respect to hybrid seed production, the availability of stored pollen for delivery to female flowers can eliminate many standard, costly practices of seed production including, but not limited to, planting male plants separately from, but in proximity to, female plants to enable hybridization, isolation of female plants from undesired pollen sources, and use of genetic or mechanical male sterility of the female plants. These practices dramatically increase field space and resources dedicated to female plants which produce seed or grain. Eliminating any one of these practices would have an immediate positive impact on seed yield per acre. Moreover, stored pollen can be applied at any time. When pollen shed from male plants and pollen receptivity of female plants fail to coincide as planned (due to management, environment, or genetic variation), application of preserved, viable pollen ensures pollination of female plants at the optimal time. Pollination by undesired external (adventitious) sources of pollen or undesired self-pollination of female plants also can be reduced or eliminated by applying stored pollen of a desired type at the appropriate time. Today, the genetics of a particular hybrid seed is determined at the beginning of a growing season by the genotype of the pollen-donating male plants and pollen-receiving female plants planted together in the field. Using the embodiments of the present disclosure, however, a hybrid seed producer responding to changing market opportunities can decide at the time of pollination to use a different male pollen (i.e., genetic source) for pollination to produce more valuable hybrid seed. Thus, stored pollen can be used to deliver unique genetic traits or genes that enhance seed quality characteristics to highly productive female inbreds. For example, traits for resistance to select insect pests which are present might be delivered. Importantly, the embodiments of the present disclosure also ensure a high level of genetic purity in the hybrid seed. As such, methods of improving pollen viability and extending the duration of its viability are of significant value to the agricultural industry.

BRIEF DESCRIPTION OF THE FIGURES

FIG. 9 shows the data collected from working example 10. The experiment measured the viability of maize pollen stored with different ratios of a medium comprising lactose and 4% Aerosil®. An unmixed control sample was used for comparison purposes. The figure shows the viability of the pollen on day 0, 4, 6, 10, 12 and 17 during the storage period.

SUMMARY OF THE INVENTION

Figure 1:
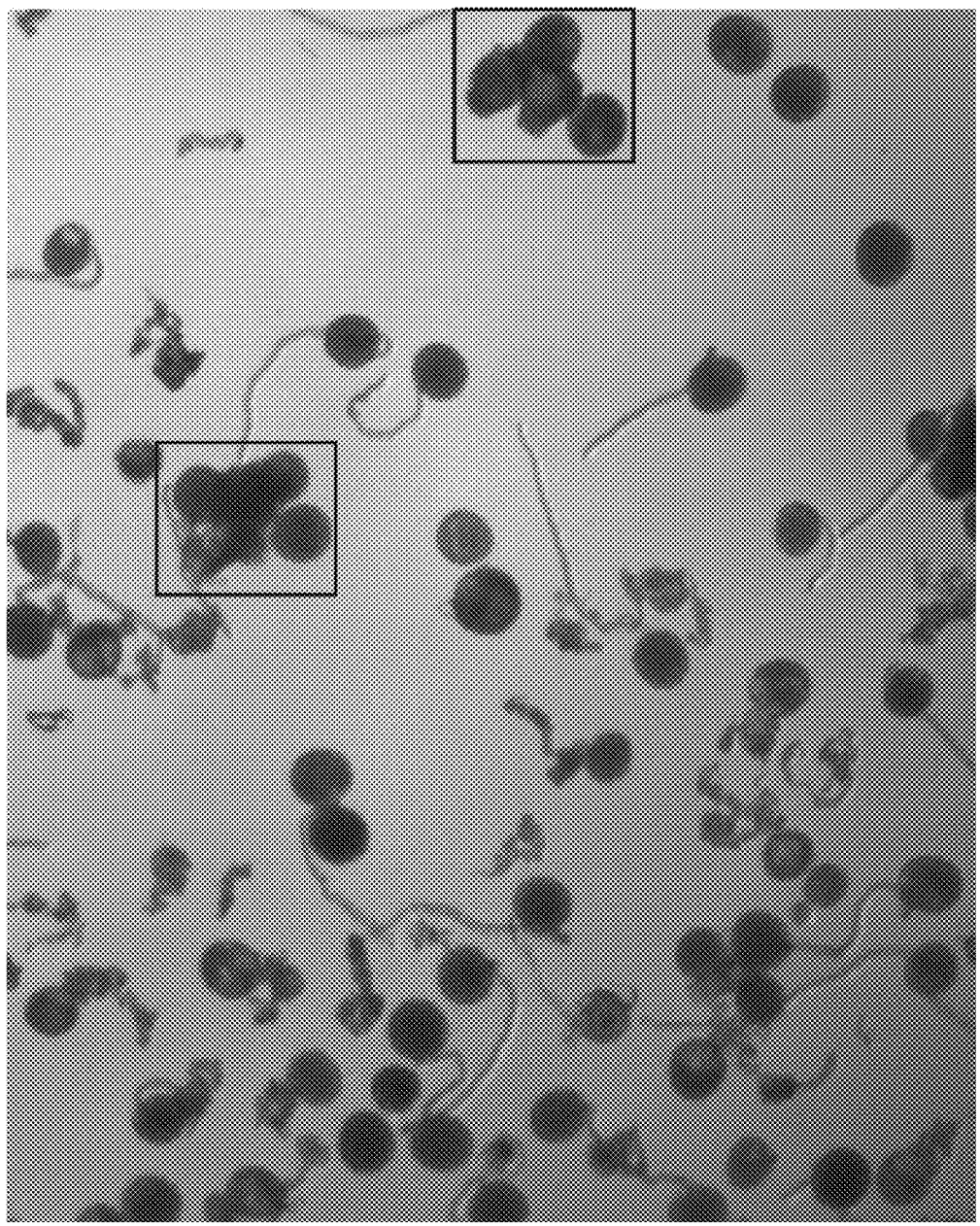
FIG. 1 shows an image of pollen grains resting in artificial growth media as described in working example 1. The image demonstrates that pollen that clusters together has a lower overall germination rate in comparison to individual pollen grains that are not in contact with other pollen grains. Two clusters of pollen are marked on the image inside boxes. Note that these clusters do not show strong pollen tube growth.

Provided is a method of preserving a plurality of pollen grains comprising preventing dead pollen contents from interacting with live pollen grains. In some embodiments, the method may include storing pollen grains with at least one substance which prevents dead pollen contents form interacting with live pollen grains. The substance may be a solid, liquid, gas, or combinations thereof. Moreover, the substance may surround at least one pollen grain, such as by minimizing surface-to-surface contact between the plurality of pollen grains. Pollen moisture content may be maintained at 15-60%, such as 35-60%. In addition, the pollen grains and the substance may be mixed, such as by continuous mixing. The ratio of the substance to pollen grains may be at least 3:1. Further, the size of the substance may range from a minimum of ten times smaller than the size of the pollen grains to a minimum of ten times larger than the size of the pollen grains. In some embodiments, the substance may include particles of varying sizes. The substance may be selected from the group consisting of lactose, Sipernat® 50, Sipernat® 50S, Sipernat® 2200, Sipernat® 22, Sipernat® 22S, Sipernat® 340, Sipernat® 350, Perkasil® SM660, Jojoba beads, Aerosil® 200, Syloid® 244, and combinations thereof. The method may include pollen which has been freshly collected, stored, or combinations thereof. Moreover, the method may include field conditioning the pollen.

In another embodiment of the invention, a method is provided wherein pollen grains are mixed with a substance wherein the substance causes the pollen grains to have a pollen moisture content of 15-60%. In some embodiments, the pollen moisture content may be 35-60%, such as 45-55%. The substance may be hydrophilic and may further prevent dead pollen contents from interacting with live pollen grains. Moreover, the method may include reducing pollen moisture content after pollen collection to less than 60%.

Glossary

"Chamber" is used herein to mean an enclosure suitable for containing and storing pollen.

"Dead Pollen Contents" is used herein to mean any material related to a dead or dying pollen grain, including but not limited to the pollen grain itself and material leaked from a dead or dying pollen grain.

"Female plant" is used to mean a plant that is being used as the recipient of pollen, and which has receptive flowers that are being fertilized.

"Fertile" or "fertility" is used to describe the ability of pollen to deliver the sperm nuclei to the ovule and thereby effect double fertilization. In flowering plants, the term "double fertilization" refers to one sperm nucleus fusing with the polar nuclei to produce the endosperm tissues, and the other sperm nucleus fusing with the egg nucleus to produce the embryo.

"Fresh" when applied to pollen means pollen released from the anthers of a flower which, in its natural pattern of organ growth and development, releases pollen upon dehiscence in response to promotive environmental conditions.

"Germinability" refers to the ability of pollen to germinate and form a pollen tube.

"Longevity," when applied to pollen, is used describe the length of time that pollen remains both viable and fertile.

"Loss of viability" is a pollen characteristic that means that the viability level of the pollen has fallen to a level below that required for successful initiation of seed development.

"Loss of fertility" is a pollen characteristic that means that the fertility level of the pollen has fallen to a level below that required for successful initiation of seed development.

"Male plant" means a plant from which pollen is collected from for use in pollinations.

"Preservation" means any storage of collected pollen that results in a level of viability, fertility, or both, which is different than the level of viability, fertility or both, which would occur if the pollen were held in unregulated conditions.

"Storage" means any period of pollen containment with the intent of using the pollen at a later time and/or date.

"Surface-to-surface contact" between pollen grains means the touching of any part of the surface area of one pollen grain to the surface area of one or more other pollen grains.

"Viable" or "viability" is used to describe pollen that is able to germinate and grow a pollen tube to at least a length twice the diameter of the pollen grain or pollen which has been judged viable by demonstration that the cellular nature of the material remains integral and is judged to maintain intactness such that normal cellular processes of metabolism and intracellular functioning is possible. The viability of pollen can be assessed in numerous ways, including, but not limited to, assessment of pollen tube growth on artificial media or excised stigmas or styles, assessment of cellular intactness by vital staining of numerous sorts, absence of electrolyte (e.g., potassium) leakage, and impedance flow cytometry. Viability can refer to a single pollen grain or a population of pollen grains. When a percentage value is used to describe pollen viability, the value is typically being applied to a population of pollen.

"Viability window" refers to the lifespan during which pollen remains viable when exposed to unregulated conditions.

"Vigor" refers to pollen performance, such as speed of germination and tube growth.

DETAILED DESCRIPTION

The following is a detailed description of embodiments of technology and methods of storing and/or preserving pollen which enable improved and/or extended viability of collected pollen by subjecting it to specialized storage conditions and techniques. The pollen may be collected from actively shedding plants or, alternately, the pollen may have been previously collected and stored according to other methods known in the art now or in the future. Such methods include, for example, freezing, freeze-drying, storing in liquid nitrogen, etc.

According to one embodiment of the invention, in order to preserve pollen with improved and/or extended viability, a plurality of pollen grains include dead pollen contents and live pollen grains and the dead pollen contents are prevented from interacting with the live pollen grains. Said another way, the invention provides partial or total isolation or separation between pollen grains and each other as well as dead pollen contents. In many embodiments, the pollen is maintained in a manner that minimizes surface-to-surface contact between individual pollen grains. As discussed in more detail in this disclosure, when pollen grains are in contact with other pollen grains, particularly for a period of time that would be typical for storage purposes, pollen grains which are losing or have lost viability negatively impact the fertility and viability of otherwise healthy pollen grains. Examples 1-3 hereinbelow are illustrative of this concept. In example 1 and the accompanying figure, it is noted that pollen which clusters together is often not viable. Moreover, examples 2 and 3 show that dead pollen mixed with fresh pollen negatively impacts the fresh pollen such that viability is decreased.

Accordingly, dead pollen contents have proven to be infectious agents that cause live pollen grains to die more quickly than they would if the live pollen grains were separated from the dead pollen contents. This may imply leakage or some kind of transfer of cell contents that are infectious out of the dead or dying pollen grains. Therefore, without being bound to a particular theory, the inventors have discovered that when pollen grains are in the process of dying or have died, leakage of pollen contents likely occurs. This leakage interacts with other pollen grains and causes their death or loss of viability, also. The present invention seeks to minimize and/or prevent such interaction. Accordingly, the invention includes separating dead pollen contents from live pollen grains. Such collected pollen may be stored for any length of time, including but not limited to just long enough to transfer pollen to a plant in the same or a neighboring field, minutes, hours, days, weeks, months, and/or years. In preferred embodiments of the invention, the disclosed method uses substances to separate dead pollen contents from live pollen grains, thus preventing interaction between dead pollen contents and live pollen grains. Such separation may occur via, but is not limited to, solid particles, liquid, flowing air or gases, reduced gravity, or storage wherein pollen grains are isolated from each other. In many embodiments, surface to surface contact between grains of pollen and/or the cellular content of grains of pollen is prevented or limited. For the purposes of this invention, the pollen can be stored in a chamber. The chamber can vary in size and material of construction. The chamber may be of any size that is suitable for containing a quantity of pollen, and may be any kind of tube, container, cartridge, vessel, enclosure, or space in which pollen is being stored, wherein the space serves as a chamber for the storage of quantities of pollen. In some embodiments, the chamber may also contain solid particles, liquid, and/or gas which minimizes the surface-to-surface contact of pollen grain surfaces.

It is beneficial, although not required, if the substance(s) employed in method of the present invention meet one or more criteria in addition to separating dead pollen contents from live pollen grains. First, it can be beneficial if the substance regulates pollen moisture content. As discussed below in more detail, certain hydrophilic substances can accomplish this goal. Furthermore, the substance may provide increased flowability when the pollen is applied to a female plant, such as for mechanical application. It is also desirable if the substance is cost effective for large scale operations, which is one benefit of solid substances or particulates generally. Another benefit of solid particulates is that they are more easily portable or transportable, which can be especially beneficial when the method will be performed on pollen as it is collected, such as in a field. It is also preferred that the substances are not harmful to the plant and/or the environment. Furthermore, it is preferred that the substance does not interact and/or communicate with the female plant onto which the pollen, combined with the substance in many embodiments, will be applied. For example, it can be beneficial if the substance does not interact with the stigma of the female plant. Similarly, it is beneficial if the substance and the pollen grains segregate after or immediately prior to application, such that the substance doesn't bind to the pollen and/or female plant, including but not limited to pollen receptors, for application to female plants.

In embodiments of the invention wherein a liquid is used to separate, and thus prevent interaction between, pollen grains from each other and dead pollen contents, isotonic solutions and/or oil solutions may be used. Preferably, the liquid will not react with the pollen grains. Moreover, in preferred embodiments, the liquid and pollen would be agitated to enhance separation of the pollen grains from each other and dead pollen contents. Agitation may be occasional or continuous and is preferably continuous. Preferably, pollen grains in such a solution will have no prolonged contact with other pollen grains and/or dead pollen contents. Moreover, in some embodiments, the pollen may essentially be suspended in the liquid. Example 17 illustrates successful pollen storage in Sonneborn® PD-23 mineral oil.

Similarly, in some embodiments of the invention, air or gases (collectively "gas" or "gases") may be used to separate pollen grains from each other and dead pollen contents, thus preventing interaction between dead pollen contents and live pollen grains. Preferably, the gas is flowing so as to effect agitation of the pollen grains and separate the pollen grains from each other and dead pollen contents. Agitation other than flowing of the gas may also be used, such as occasional or continuous agitation. Preferably, pollen grains in a chamber with gas will have no prolonged contact with other pollen grains and/or dead pollen contents. In some embodiments, the pollen may essentially be suspended in the gas.

In yet another embodiment of the invention, physical and/or spatial separation of the pollen may result in separation of pollen grains from each other and/or dead pollen contents, thus preventing interaction between dead pollen contents and live pollen grains. For example, pollen grains may be stored in single grain layers where there is a space between individual pollen grains. In some embodiments, the storage structure may provide a physical separation between pollen grains and dead pollen contents and/or each other. In other embodiments, the gas in the chamber may provide the separation between pollen grains and dead pollen contents and/or each other. In yet other embodiments, organic or non-organic structures may separate the pollen contents from dead pollen contents and/or other pollen grains. Therefore, the pollen grains are not in contact with each other. Of course, any type of physical separation may be used, whether known now or in the future.

As discussed above, the methods disclosed herein improve and/or extend the viability of pollen. Viable pollen can successfully germinate and commonly possesses the vigor necessary to promote fertilization and initiation of seed development. Not all viable pollen is also fertile pollen. In some cases, even when a pollen grain is viable and commences with pollen tube growth, it may lack the vigor necessary to reach the ovule and promote fertilization. Non-viable pollen grains cannot successfully germinate. Thus, in some embodiments of the present invention, pollen with good viability is desirable for use with the methods in the present disclosure. The level of viability and fertility required for successful pollinations is typically accepted or defined in the art to be an average of four grains of fresh pollen per silk, or four to eight grains of preserved pollen which has been preserved according to the methods of the present disclosure.

As discussed above, many embodiments of the present invention require pollen collection or acquiring pollen which has previously been collected. Pollen collection for the purposes of the invention may take place by any method and in any location where plants are grown, such as a growth chamber, a greenhouse, a glasshouse, a shade house, a hoop house, a vertical farming facility, a hydroponic facility, or any growing facility providing cultured tassels, as described below. Pollen may, optionally, be field-conditioned prior to storage or preservation, such as according to the methods set forth in U.S. patent application Ser. No. 15/486,737 titled Pollen Conditioning and Preservation Method, the entire contents of which are hereby incorporated by reference. Field conditioning, if used, may also take place using other methods known in the art, now or in the future. In some embodiments, field conditioning may occur immediately upon collection or at any point between collection and storage. In addition, it is anticipated that field conditioning may include methods of the present invention.

The collection of fresh pollen may be conducted in ways commonly known in the art. For example, pollen may be collected from freshly shedding flowers or male flower structures produced in any variety of manners. In the case of maize, and many other species, the plant is monoecious and contains male and female inflorescences on a single plant. In the practice of breeding, pollination, cross-pollination, and hybridization, some plants act as the male plant from which pollen is collected for use in pollinations, and some plants act as the female plant being the recipient of the pollen. In the case of self-pollinations, a single plant is acting as both the male plant and the female plant because the female flowers are fertilized by pollen from its own male flowers. Similar to self-pollinations, sib-pollinations occur when plants of the same genetics (such as a neighboring plant from the same field) act as both the male plant and the female plant. For purposes of this disclosure, the term "self-pollination" includes sib-pollinations, as the same genetics are involved in both situations. Still referring to maize as an example, pollen is collected from freshly-shedding male flowers borne on tassels, which may be attached, or detached, from the plant.

Pollen from any type of plant may be collected from plants grown in any environment suitable for plant growth. Such environments include, but are not limited to, a field, a growth chamber, a greenhouse, a glasshouse, a shade house, a hoop house, a vertical farming facility or a hydroponic facility. Alternatively, pollen may be collected directly from anthers by crushing or grinding the anthers or by letting them naturally continue to expel pollen as the anther dries, thereby releasing the pollen and allowing for its collection. In addition, pollen may be collected from a tassel culture facility (Pareddy D R, Greyson R I, Walden D B (1989) Production of normal, germinable and viable pollen from in vitro-cultured maize tassels. Theor Appl Genet 77:521-526.). Cultured tassels may be mature tassels that have been removed from plants in any type of growing facility or environment, including a field or other type of growing facilities, and placed into water in a controlled environment to collect pollen or cultured tassels may be tissue that has been harvested from flowering structures at immature stages and then cultured to develop into a tassel.

Alternatively, anthers may be collected directly, instead of pollen. Anthers may be collected prior to the pollen maturing in the anther, during the maturation time, or when the pollen is mature and being released. Whole anthers may also be stored for later use by storing them in the compositions of the invention. Pollen that is either immature, partially mature, close to mature but not yet being released, or mature dehisced pollen, may be released from collected anthers by stripping, grinding, shaking, drying, or other similar methods. In particular, grinding is effective for immature pollen because the grinding of the entire anther along with the immature pollen can be conducted in the composition of the invention. This process will automatically release the pollen into the ideal environment where the surfaces of each pollen grain are limited in their ability to touch other grains. Moreover, anthers may be stored employing methods of the present invention, including but not limited to, with solid, liquid, gas, and/or physical separation of pollen grains to separate dead pollen contents from live pollen grains.

This disclosure outlines both the methods of minimizing surface-to-surface contact between pollen grains, and the substances that are used to minimize pollen surface-to-surface contact in order to improve viability and fertility. These substances may be solid particles, liquids, or gas-based compositions, or may be combinations of solids and gases, liquids and gases, or solids and liquids. This may include switching pollen from one substance to another during storage. Moreover, a combination of substances may be used, including multiple substance of a single state (i.e. solid, liquid, and/or gas), or multiple substances of various states. Moreover, the substance may be refreshed or replaced over time, including with the same or a new substance. Accordingly, this may include switching pollen from one substance to another during storage. The term "liquid" as used herein includes gels.

Preferred embodiments of the invention utilize solid particles to separate pollen grains from dead pollen contents and/or each other, thus preventing interaction between dead pollen contents and live pollen grains. In many embodiments, the solid particles minimize surface-to-surface contact between grains of pollen. In the case of solid particle substances, preferably the size of the particles should be determined in relation to the size of the pollen grains intended to be stored. If the solid particles are too large, they can sometimes be ineffective at preventing contact between pollen grains because the pollen can collect in pockets between the particles. If the solid particles are too small, they can also be ineffective at separating the pollen grains and dead pollen contents because they do not provide enough separation. Different species of plant pollen can vary in size, ranging from approximately 6 to 100 μm in diameter. In addition, some pollen grains have surfaces that are not perfectly round which result in a larger surface area. Accordingly, using solid particle compositions that contain a range of particle sizes and/or shapes will allow use with pollen from different species. Alternatively, routine experimentation will easily determine the ideal size of solid particles based upon the size and morphology of the pollen grains to be stored, such as shown in examples 6 and 7. In one example, the size of the solid particles may be between ten times smaller than the pollen to be stored to ten times larger than the pollen to be stored. Referring to maize as an example, the preferred size of the particulate may be 20 microns. Just one example of a solid particulate of that size is Sipernat 340.

A further consideration is the ratio of solid particulate substance to pollen grains. High ratios of substance to pollen tend to increase separation between dead pollen contents and live pollen grains. Moreover, higher ratios result in dilution of the pollen, which is sometimes beneficial for application of the pollen to the female plants. In some examples of embodiments, the ratio may be anywhere from 1:1 to 1:100 of pollen grains to substance. In some examples, a ratio of 1:3 pollen grains to substance is preferred. Moreover, the ideal ratio can depend on the amount of time for which the pollen will be stored. Over the short term, the ratio has been shown to be less important. On the other hand, as time progresses, the ratio becomes more important in maintaining viability of preserved pollen. Example 10 demonstrates an embodiment wherein a ratio of 3:1 solid particulate substance to pollen grains outperforms other ratios and further describes routine testing that may be used to find ideal ratios in any type of pollen. The ratio can be optimized for benefits including, but not limited to, enhancing storage duration, deconcentrating pollen, and/or optimizing flowability.

Preferably, the nature of any solid particle compositions used to separate dead pollen contents from live pollen grains includes particles that do not cause negative interactions with the pollen. In some embodiments, the solid particles are of a non-reactive nature so that the pollen is essentially unaffected by the particles. For example, the solid particle must not remove too much moisture from the pollen because the pollen will die. The loss of moisture impacts the viability of pollen, with greater moisture loss resulting in greater viability loss, and eventually the death of the pollen grain. Examples 8 and 9 show that pollen stored with desiccants negatively impact viability. A slight hydrophilic nature can be beneficial because it can separate dead pollen contents from live pollen grains. More specifically, and without being bound a particular theory, experimentation has shown that substances that are slightly hydrophilic absorb dead pollen contents that escape or leak from dead and/or dying pollen. Because the hydrophilic substances absorb this material, it is separated from live pollen grains. Moreover, slightly hydrophilic materials help regulate pollen moisture content, which can oftentimes be important to pollen viability. Slightly hydrophilic substances often do not desiccate pollen in the same way that more hydrophilic substances may. Hydrophobic particles may be less desirable because they may have a natural tendency to avoid physical contact with the pollen grains which could result in a gradient between the pollen and the particle. Nonetheless, some hydrophobic substances can be beneficial. Namely, some hydrophobic substances may attach to the surface of pollen grains and at least partially coat the grains. Such coating can result in separation of dead pollen contents from live pollen grains and/or separation between living pollen grains.

Accordingly, pollen moisture content and regulation of same is beneficial in certain embodiments of the invention. In some examples of embodiments, the method may include pollen moisture content at 15-60%. More specifically, pollen moisture content may be 40-58%. In even further embodiments, pollen moisture content may be 45-55%. In some embodiments of the invention, it has been found that the pollen can be kept at higher moisture levels than has previously been considered optimal in the art. Accordingly, in some embodiments, it can be beneficial if substance used in the invention can enable maintenance of higher pollen moisture content without detriment.

Solid particles that can be useful for the disclosed invention include, but are not limited to, inorganic particles, organic particles, dormancy regulators, osmotic regulators, cellular respiration inhibitors and disruptors, electron transport inhibitors, uncouplers of membrane electron transport, membrane stabilizers and conditioners, cell wall stabilizers and conditioners, growth regulators, plant hormones, cryoprotectants, monosaccharides, disaccharides, polysaccharides, anti-flocculants, dispersal agents, bentonite, potato starch, corn starch, cellulose, sand, desiccants, flow agents, mineral oil, paraffin oil, sugars in liquid, dry sugars, water, and activated charcoal. It is to be understood that the selection of the solid particles to be used may be influenced by the type of pollen to be stored. For example, the selection may be based on size and/or how tolerant specific pollen is to certain interactions and characteristics. An ideal composition may include a single solid particle type or a combination of particle types that are chosen to maximize pollen viability and longevity. It may also contain a range of particle sizes to ensure that both larger and smaller grains of pollen are being separated with equal efficiency. Routine experimentation can be conducted in accordance with examples 4 and 5 to determine the best particle or particle blend for storage purposes.

In addition, it may be beneficial to add a substance that will increase flowability of the stored pollen such that the pollen can be easily applied to plants at a later date. Such a compound must not cause negative interactions between other solid particles in the storage medium, nor between the pollen grains. Examples of compounds that separate dead pollen contents from live pollen grains and also aid in flowability include, but are not limited to, Sipernat® 50, Sipernat® 50S, Sipernat® 2200, Sipernat® 22, Sipernat® 22S, Sipernat® 340, Sipernat® 350, Perkasil® SM660, Jojoba beads, Aerosil® 200, Syloid® 244, isotonic buffers, oils, and gases.

In yet another embodiment, the substance may be empty pollen grains. Namely pollen grains that have been washed free or otherwise emptied of their internal composition may be used to separate dead pollen contents from live pollen grains, thereby preventing interaction between the two.

The use of liquid or gas to prevent surface-to-surface contact between pollen grains can also be used to achieve the aims of the invention. In such cases, interaction between dead pollen contents and live pollen grains is prevented. In the case of gases, a constant flow of gas through the chamber containing the pollen suspends the grains and minimizes any contact that would otherwise be experienced due to lack of flow. In the case of pollen storage in liquid, buffers which are isotonic do not readily exchange fluid across the pollen membrane serve as an excellent storage medium. Similarly, hydrophobic solutions such as mineral oil also minimize fluid exchange across the membrane.

Pollen can be subjected to additional preservation steps in order to increase its ability to retain viability and fertility over storage periods. The preparation of pollen for storage requires a careful process including an environment with known relative humidity levels, as well as specific temperature and atmospheric pressure conditions. For example, the temperature may be 1° C. to about 10° C. In some embodiments, relative humidity may be 50-100%. Moreover air pressure may be 15 kPa-150 kPa. In addition, the presence of useful gases will assist in maximizing storage success. Useful gases may include but are not limited to nitrogen, carbon dioxide, nitrous oxide, oxygen, or a mixture of these gases.

Optionally, during the period of pollen storage, the pollen contained within the chamber may be agitated mechanically. Agitation may be occasional or continuous. In preferred embodiments, agitation is continuous. The agitation serves to expose the maximum surface area of the pollen to the additives in the chamber, whether solid, liquid or gas, thereby ensuring a homogenous mix of the pollen with the additive, and preventing surface-to-surface contact of pollen grains, clumping of the pollen, and the spread of necrosis in the event that some pollen grains die. Experimental data, particularly examples 2 and 3 below, has shown that when live pollen grain surfaces contact the surfaces of dying or dead pollen grains, the live pollen is negatively impacted and will subsequently die. The continued, regular, and/or occasional agitation of pollen grains in the composition, including dead or dying pollen grains, may be achieved in a number of different ways, including the use of vibration, forced air, rotation, mixing, or other means.

As explained in detail in the preceding paragraphs, maximizing and extending the viability of pollen using the disclosed method requires careful manipulation of one or more of a number of factors within defined ranges. Laboratory-generated data using maize pollen as a test species have indicated the conditions for improving pollen viability include modification of one or more conditions within the chamber to fall within the disclosed ranges as set forth below.

The temperature of the chamber containing the pollen within the composition may be maintained from about 1° C. to about 10° C., including about 1° C., about 2° C., about 3° C., about 4° C., about 5° C., about 6° C., about 7° C., about 8° C., about 9° C. and about 10° C. While lower temperatures are often preferable, this invention also has the ability to maintain and/or increase pollen viability at ambient and/or high temperatures, which has heretofore been unknown in the art. Namely, according to Lyakh, et. al., Euphytica 55: 203-207, 1991, heating of mature pollen at 35 degrees Celsius decreased maize pollen grain viability even at very short exposure (3-5 min). Nonetheless, as shown in example 16 below, methods of the present invention are able to maintain and or increase maize pollen viability at temperatures as high as 32.8 degrees Celsius with considerable success. Accordingly, methods of the present invention may include pollen stored at any temperature. In some examples of embodiments, high and/or ambient temperature methods may be conveniently used in the field and for transport.

In examples of embodiments, pollen subjected to the disclosed method may be used in any application where pollen is a commercial or experimental unit. In one example, the preserved pollen may be used to produce seed, hybrid, parent, or otherwise, in any setting, including but not limited to a laboratory, greenhouse, and field. In another example, the pollen may be used to produce grain, hybrid or otherwise, in any setting, including but not limited to a laboratory, greenhouse, and field. Moreover, as discussed above, such a method may be applied to pollen from the Poaeceae (Gramineae) family of plants, as well as any other plant species wherein it is desired to use pollen.

The preservation techniques disclosed in this invention are intended to successfully preserve pollen such that the preserved pollen maintains its viability to the extent that about 4 to about 20 grains of pollen are sufficient to successfully pollinate an embryo.

Although various representative embodiments of this invention have been described above with a certain degree of particularity, those skilled in the art could make numerous alterations to the disclosed embodiments without departing from the spirit or scope of the inventive subject matter set forth in the specification and claims. In some instances, in methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to the embodiments outlined above, various alternatives, modifications, variations, improvements and/or substantial equivalents, whether known or that are or may be presently foreseen, may become apparent to those having at least ordinary skill in the art. Listing the steps of a method in a certain order does not constitute any limitation on the order of the steps of the method. Accordingly, the embodiments of the invention set forth above are intended to be illustrative, not limiting. Persons skilled in the art will recognize that changes may be made in form and detail without departing from the spirit and scope of the invention. Therefore, the invention is intended to embrace all known or earlier developed alternatives, modifications, variations, improvements, and/or substantial equivalents.

The following examples illustrate the present invention in more detail and are illustrative of how the invention described herein could be implemented in pollen of various species.

EXAMPLE 1

Experimentation has demonstrated a correlation between pollen density and its ability to successfully form a pollen tube. Placing pollen into an artificial liquid medium is a common practice for measuring pollen grain viability.

With the artificial liquid germination media playing a key role in determining pollen viability, thousands of assays have been performed to test the viability of stored pollen during the development of the invention in this disclosure. Throughout this experimentation, it has been noted that pollen which clusters together in the artificial liquid germination medium has a lower overall germination rate when compared to the pollen which is not in direct contact with other grains of pollen. FIG. 1 demonstrates clusters of pollen grains which do not successfully form tubes. This observation has fueled the development of compositions for pollen storage that prevent the pollen grains from touching each other and that separate live pollen grains from dead pollen contents and/or other live pollen grains, thereby preventing any negative impact such touching may generate.

EXAMPLE 2

In order to assess the negative impact that dead or dying pollen has on fresh pollen, several methods of producing dead pollen were tested to observe the impact on fresh pollen. Each batch of dead pollen was mixed with freshly collected pollen samples.

A batch of 20 mL of freshly-shed maize pollen was collected and equally divided into five different 50 mL centrifuge tubes, of which two were control tubes. The pollen samples were subjected to three different treatments that would kill the pollen. The first sample was poured into a glass test tube which was then placed into a heating block set at 95° C. for a duration of 5 minutes. The charred appearance of the pollen made it look carbonized and very little moisture content was visually detectable within the sample. For the second treatment, freshly collected pollen was placed into a glass test tube and microwaved for a period of 1 minute. The microwave is frequently used as a means to create a kill step on the Amphasys flow cytometer. The microwave disrupts the cell membrane causing the cytoplasmic contents to spill out, thereby killing the pollen. For third treatment, freshly collected pollen was placed into a glass test tube which was then placed into a heating block set for 95° C. for a duration of 3 minutes. The pollen was semi-carbonized in appearance and the sample was less charred than the carbonized treatment. For a fourth treatment, a different source of pollen was used. This pollen had been collected a month prior and had been allowed to thoroughly dry at 21° C. and 50% relative humidity for a period of more than 30 days. Because maize pollen has a very short life span at such conditions, this pollen was expected to be completely dead.

Another collection of freshly shedding pollen was made. The fresh pollen was added in an equal volume to each of the four treated pollen samples described above. Each tube was shaken to thoroughly mix the contents, allowed to rest for 10 minutes and then applied to silks by applying the contents of the tube over fresh silks.

Figure 2:
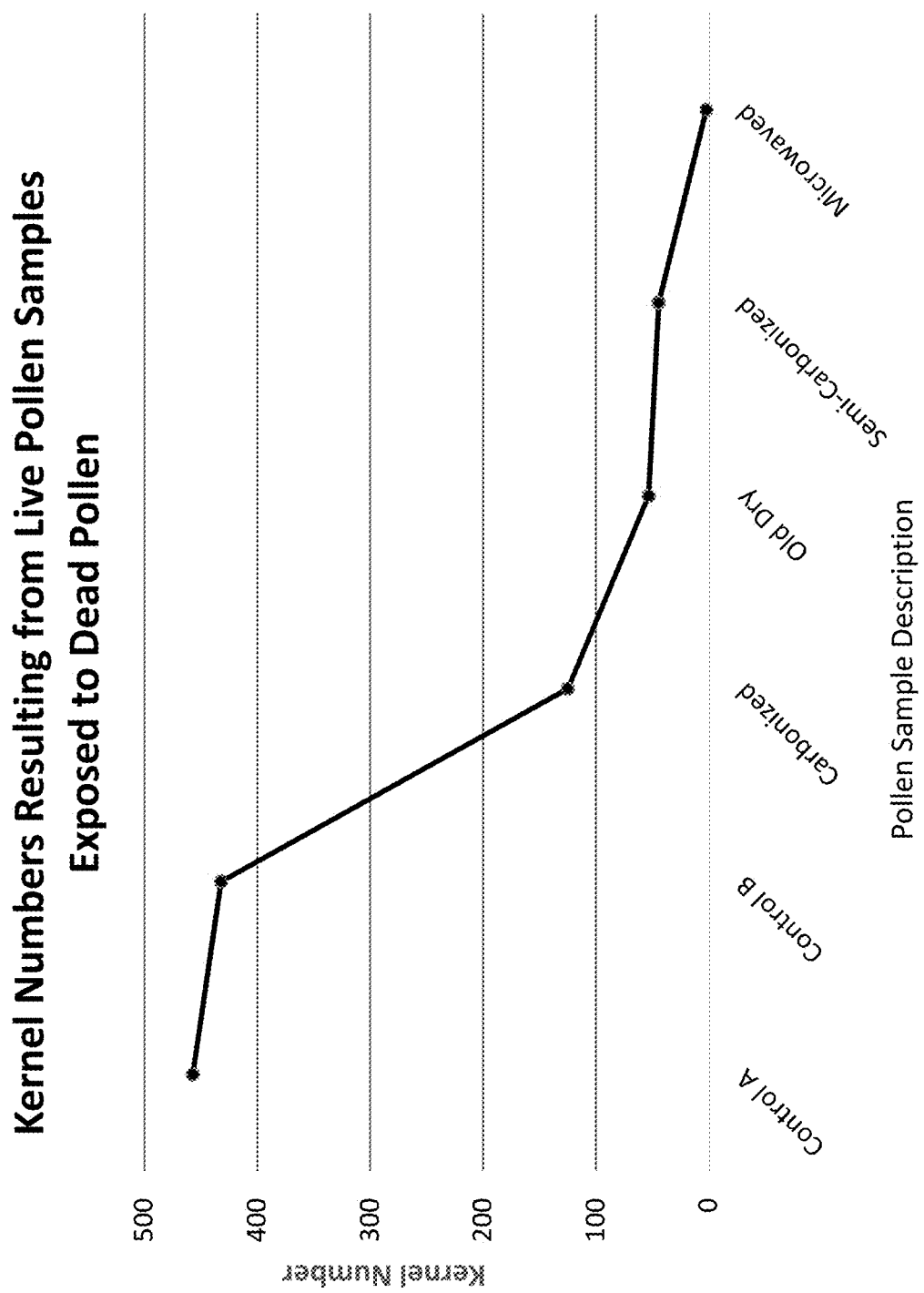
FIG. 2 shows the impact that dead or dying pollen has on fresh pollen as described in working example 2. Two control samples were tested as well as four samples that contained pollen that had been subjected to treatments that would cause pollen death.

The pollinated ears were allowed to mature over the course of several weeks and then harvested. For each treatment, the number of kernels per ear was counted and recorded. In summary, the data in FIG. 2 shows that when they are mixed together, dead pollen resulting from various treatments drastically impacts the viability of healthy pollen.

The microwaved pollen had the greatest impact on overall fresh pollen viability, producing an average of just over 2 kernels per ear. The semi-carbonized pollen was the next to lowest followed by the old dry pollen. Finally, the carbonized pollen showed the least amount of impact, but still a very large reduction in pollen viability. It is evident that maintaining fresh pollen in a healthy, viable state requires maintaining separation between pollen grains, and in particular preventing the interaction of healthy pollen with dead or dying pollen.

EXAMPLE 3

In order to further assess the negative impact that dead or dying pollen has on fresh pollen, several tests were conducted to observe the impact of dead pollen on fresh pollen as well as 4-day-old pollen. Each batch of dead pollen was mixed with freshly collected pollen samples.

Figure 3:
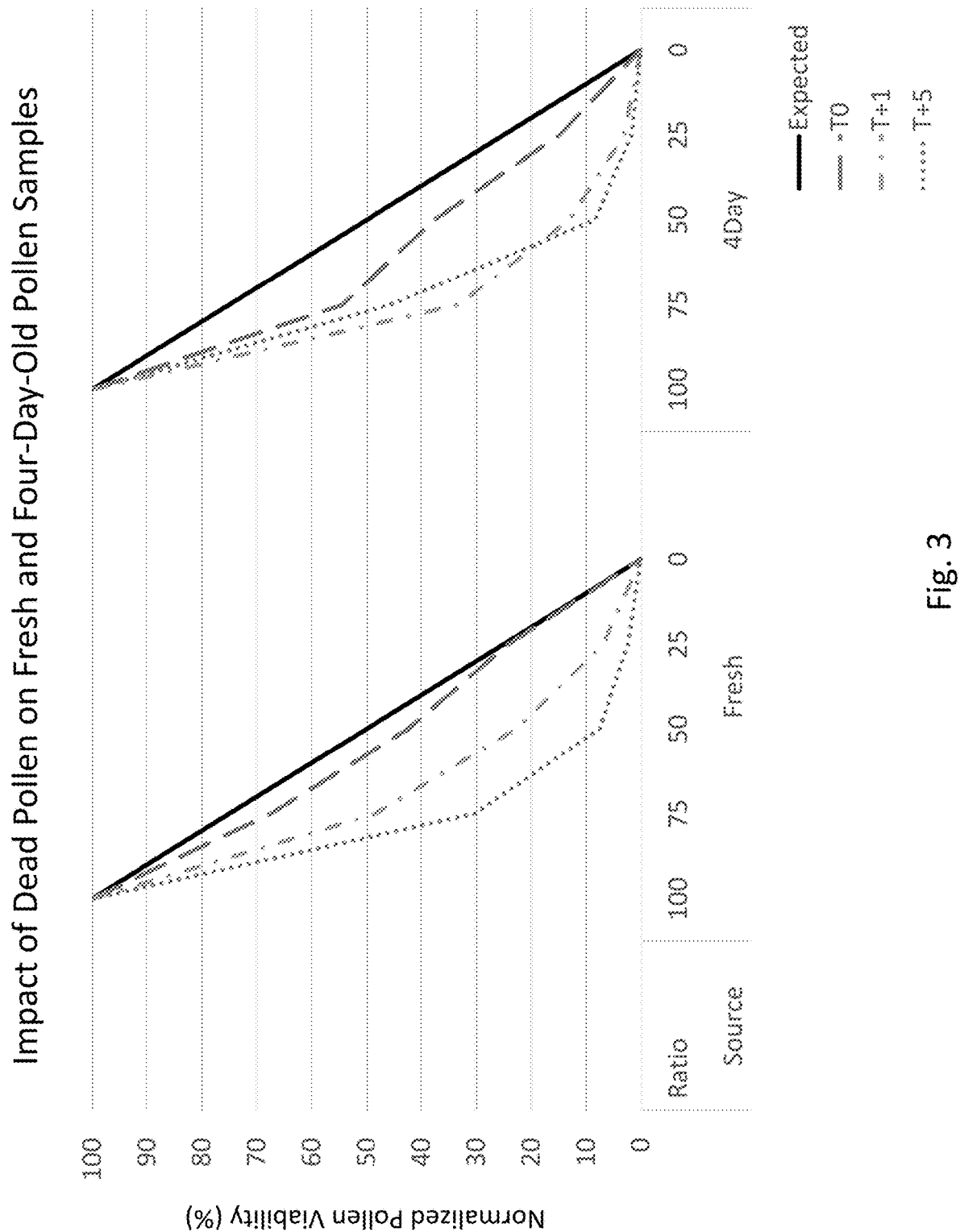
FIG. 3 shows the impact of dead pollen on fresh pollen and four-day-old pollen as described in working example 3. The figure demonstrates the negative impact that dead pollen has on live pollen, causing a rapid decline in viability. The figure shows that dead pollen has a more significant effect on pollen that has already begun to deteriorate.

Freshly collected pollen and 4-day-old pollen were divided into four samples of each. Maize pollen that had been allowed to dry for a period of over 30 days (and was therefore dead) was then added to 3 of the 4 tube sets. The first tube was used as a control and had no dead pollen added to it. The second tube set was mixed with a 75:25 ratio of live to dead pollen. The third tube set was mixed with a 50:50 ratio of live to dead pollen. The fourth tube set was mixed with a 25:75 ratio of live to dead pollen. Viability scores were obtained using Amphasys at time zero, 24 hours and 5 days. This data is shown in FIG. 3. In order to give each data set equal relativity, the time zero viability scores were normalized to 100 percent viability and the expected rate of pollen viability loss was plotted in a linear form. After 24 hours, the viability scores taken using Amphasys indicated that at each mix ratio, the dead pollen was causing an exponential decay of health that greatly exceeded linear form. The trend was also noted that the higher the ratio of dead pollen to live pollen, the faster the decline in overall health of the sample occurred. Finally, the overall decline in health in the 4-day-old sample set was much more pronounced than the fresh pollen tube set, indicating that pollen which has already begun to deteriorate is more affected by the addition of dead pollen than fresh pollen samples.

EXAMPLE 4

Figure 4:
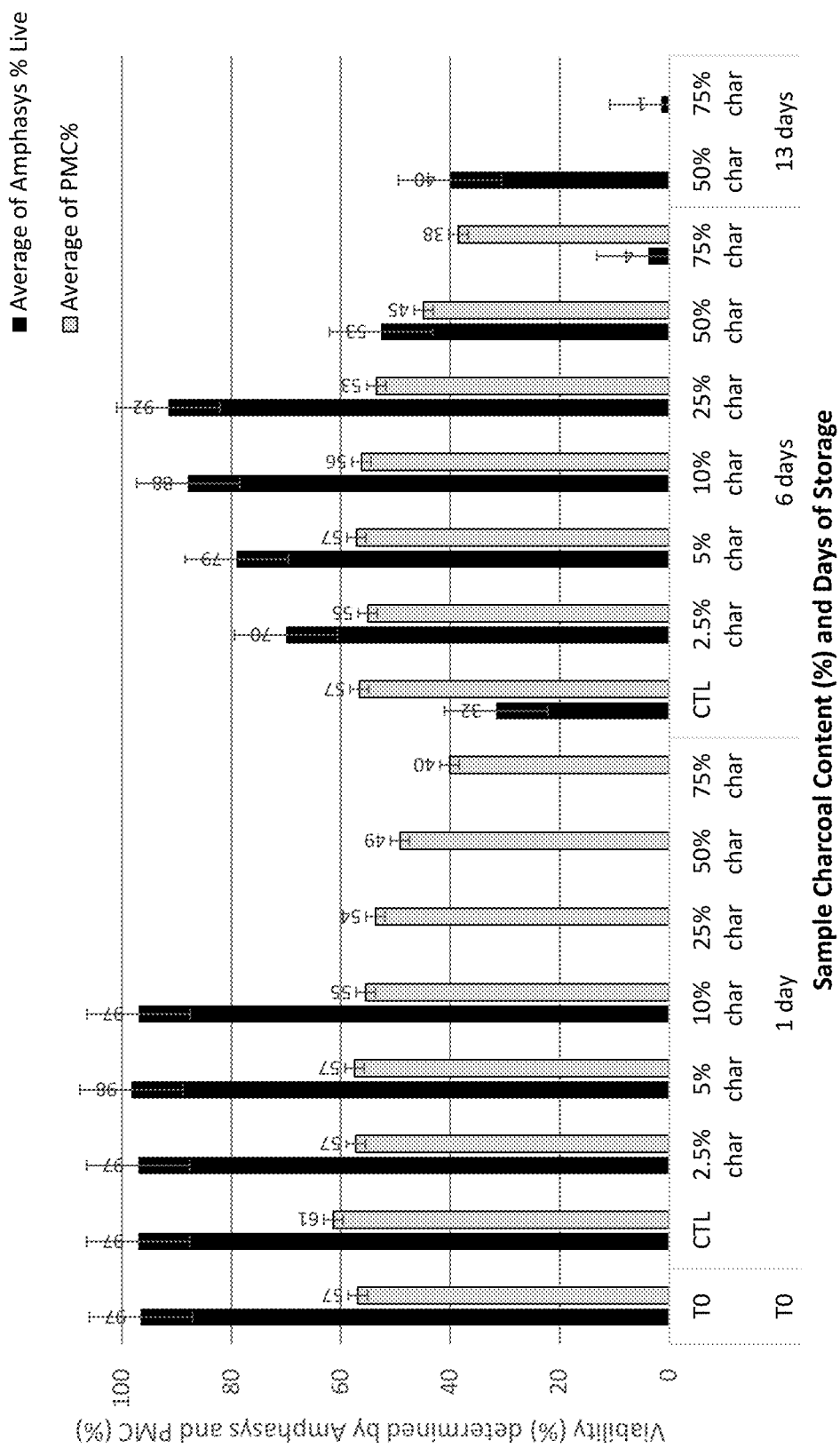
FIG. 4 shows the data collected from working example 4. The experiment used maize pollen collected from the field and stored in particulate charcoal. The pollen was mixed with charcoal at various percentages ranging from 2.5 to 75% charcoal. The figure shows the results of viability and pollen moisture content (PMC) testing after 1 and 6 days of storage.

In initial experiments considering different types separation compounds to use for pollen storage, experiments were conducted using activated charcoal as a separator. Field pollen was hand collected from various maize genotypes, and temporarily stored in 50 mL conical tubes, at 5° C. T0 Amphasys was conducted along with pollen moisture content (PMC) determination of the unmixed control pollen. Amphasys provides a reliable determination of pollen viability using an impedance flow cytometer, which measures the electrical properties of pollen grains. Viability at T0 was 97% with a PMC of 57% using the standard overnight oven method. The pollen was mixed with charcoal powder (activated charcoal) at various percentages. Activated charcoal is often used to absorb toxic substances. Mixed samples were then stored at 5° C., in uncapped 50 mL tubes. Timepoint data was collected at days 1 and 6, using Amphasys when the concentration of charcoal would allow. Small quantities of sample were suspended in Ampha 6 media and then filtered with a 150 μm filter to remove any large particles that might affect the fluidics on the Amphasys. As shown in FIG. 4, the percent of charcoal influenced both the viability of the pollen and the pollen moisture content (PMC). Used in lower quantities, 2.5-25% in this case, viability remained as high as 92% at 6 days storage. However, issues with poor flowability were noted as samples became fluffy and were aggregating by day 6.

EXAMPLE 5

Figure 5:
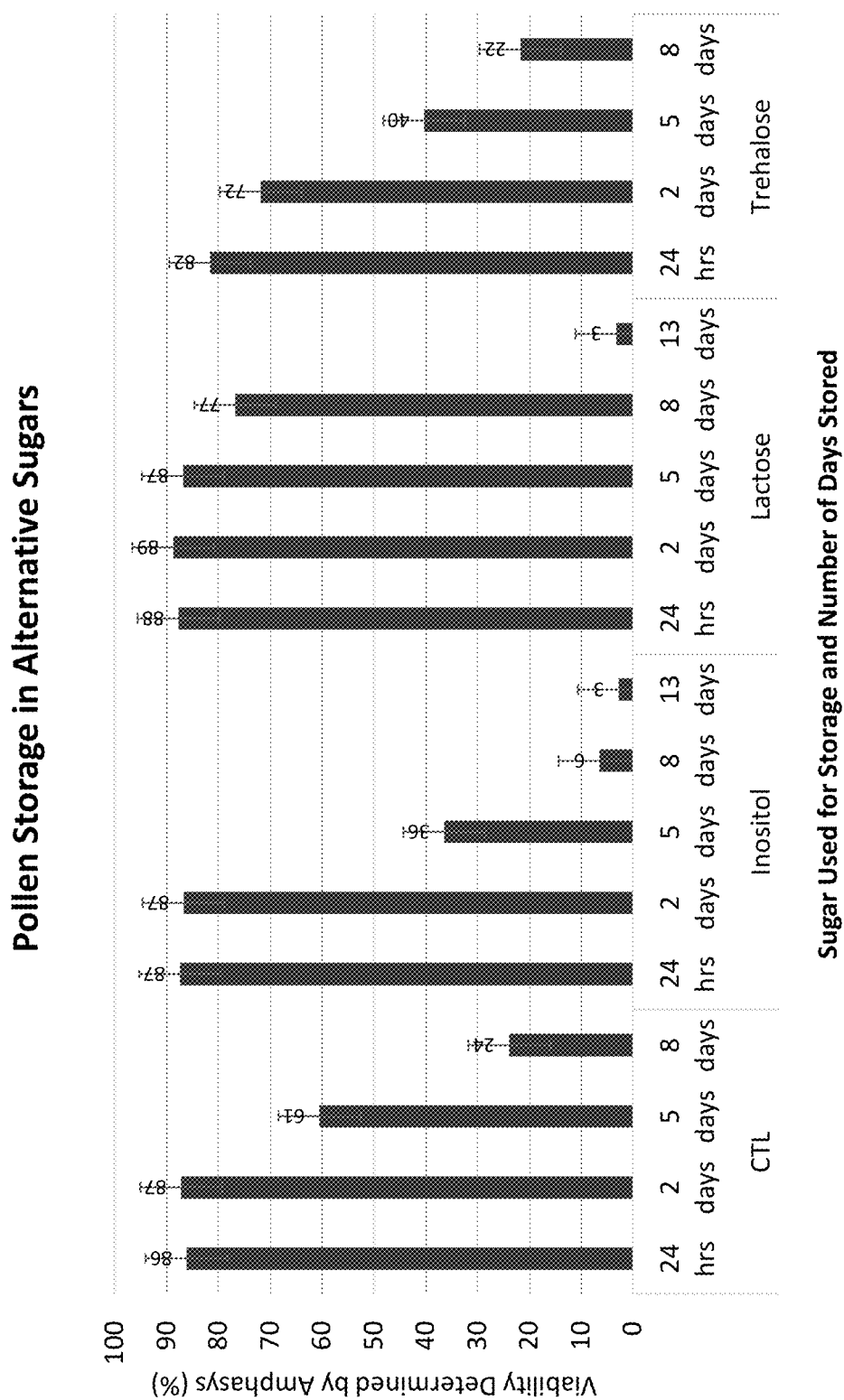
FIG. 5 shows the data collected from working example 5. The experiment measured the viability of maize pollen collected from a greenhouse and stored with various sugars. The pollen was mixed at a 1:1 ratio with the sugar media for each sample. The figure shows the viability of the pollen after 24 hours, 2, 5, 8 and 13 days.

In continued efforts to test different substances for the purposes of pollen grain separation, an experiment was conducted with a series of different saccharides to determine efficacy for pollen grain separation and preservation. Mixed pollen was collected from various actively-shedding maize plants grown in the greenhouse. Hand collection was done with a funnel and screen to remove anthers. The bulk pollen sample was divided into four equal portions, each of which was approximately 5 mL in volume. Each sample of pollen was stored in a capped 50 mL conical tube at 5° C. overnight and its viability was tested using Amphasys roughly 24 hours after collection. A 1:1 volume ratio of one of three different types of sugars was added to each tube so that the amount of sugar was equal to the amount of pollen in each tube. The tube was then inverted multiple times to thoroughly mix the sugar with the pollen. Tube 1 contained a 1:1 mix of maize pollen to inositol, tube 2 contained a 1:1 mix of maize pollen to lactose, and tube 3 contained a 1:1 mix of maize pollen to trehalose. Tube 4 served as a control with 5 mL of pollen. Each tube was capped and stored in a 4° C. environment. Amphasys viability data from a small aliquot of each tube was collected at timepoints 24 hours, 2, 5, 8, and 13 days. This data is presented in FIG. 5.

After 24 hours of storage, the viability of the trehalose sample showed a slight decline in viability when compared to the other samples. Day 2 showed a sharper decline in the trehalose sample viability when compared to the other 3 samples. Day 5 showed a sharp decline in viability for all samples with the exception of lactose. Day 8 provided a very clear indicator that lactose was showing good pollen preservation, with 77 percent viability as compared to 24 percent in the control. Based on the overall results, it was determined that saccharides can be suitable separation compounds for keeping pollen grains separated from each other while maintaining viability, and that lactose was particularly suitable for keeping grains of maize pollen both separated from each other and viable. It was also noted that the pollen in the lactose sample was slightly clumpy in nature, with the pollen not flowing as freely as freshly harvested pollen.

EXAMPLE 6

Figure 6:
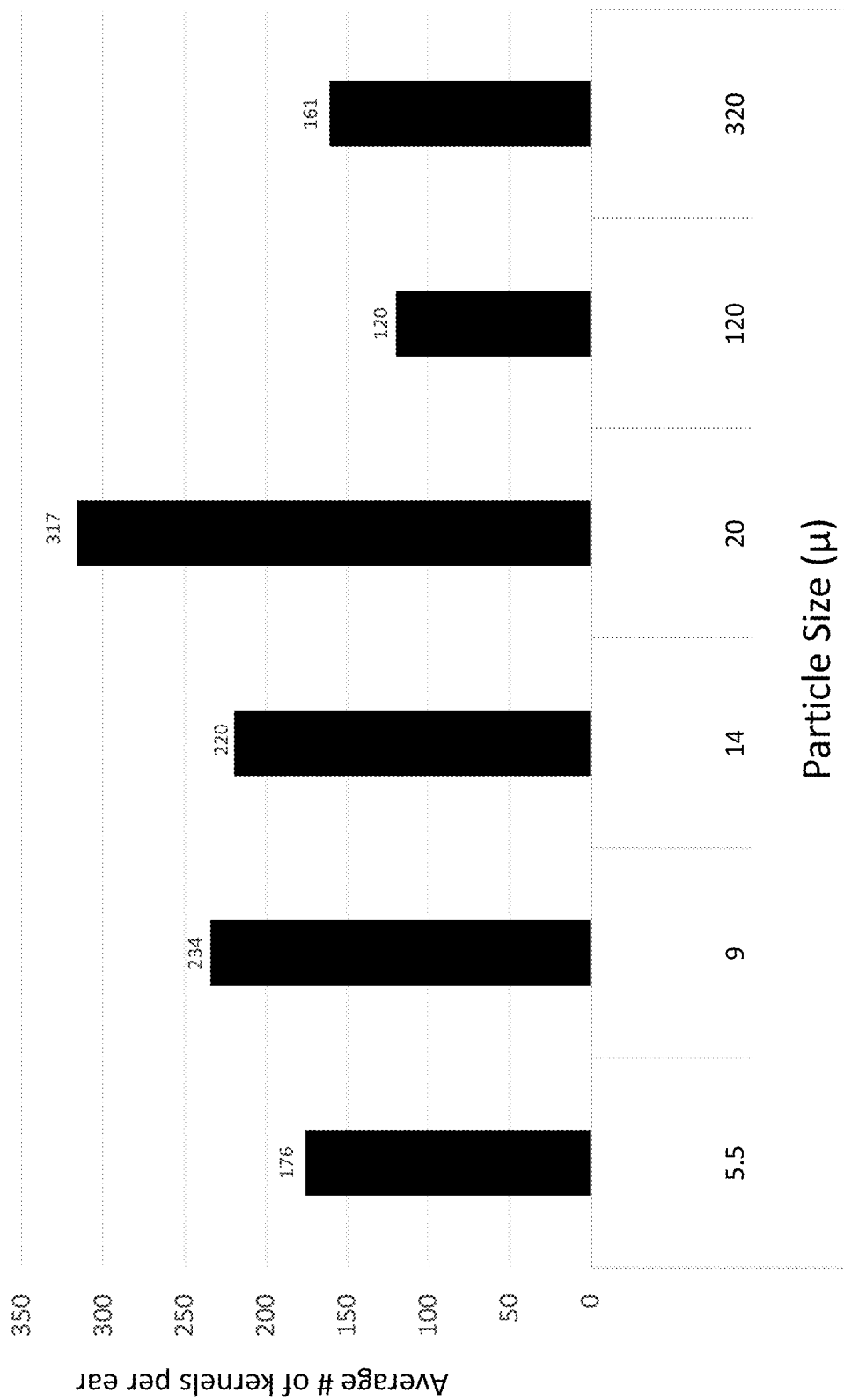
FIG. 6 shows the data collected from working example 6. Pollen was stored in silica particles of different sizes to determine the effect of particle size on storage of pollen and its viability. Following storage for 24 hours in the silica particles, the pollen was used to conduct hand pollinations. The figure shows the kernel set for each sample.
Figure 7:
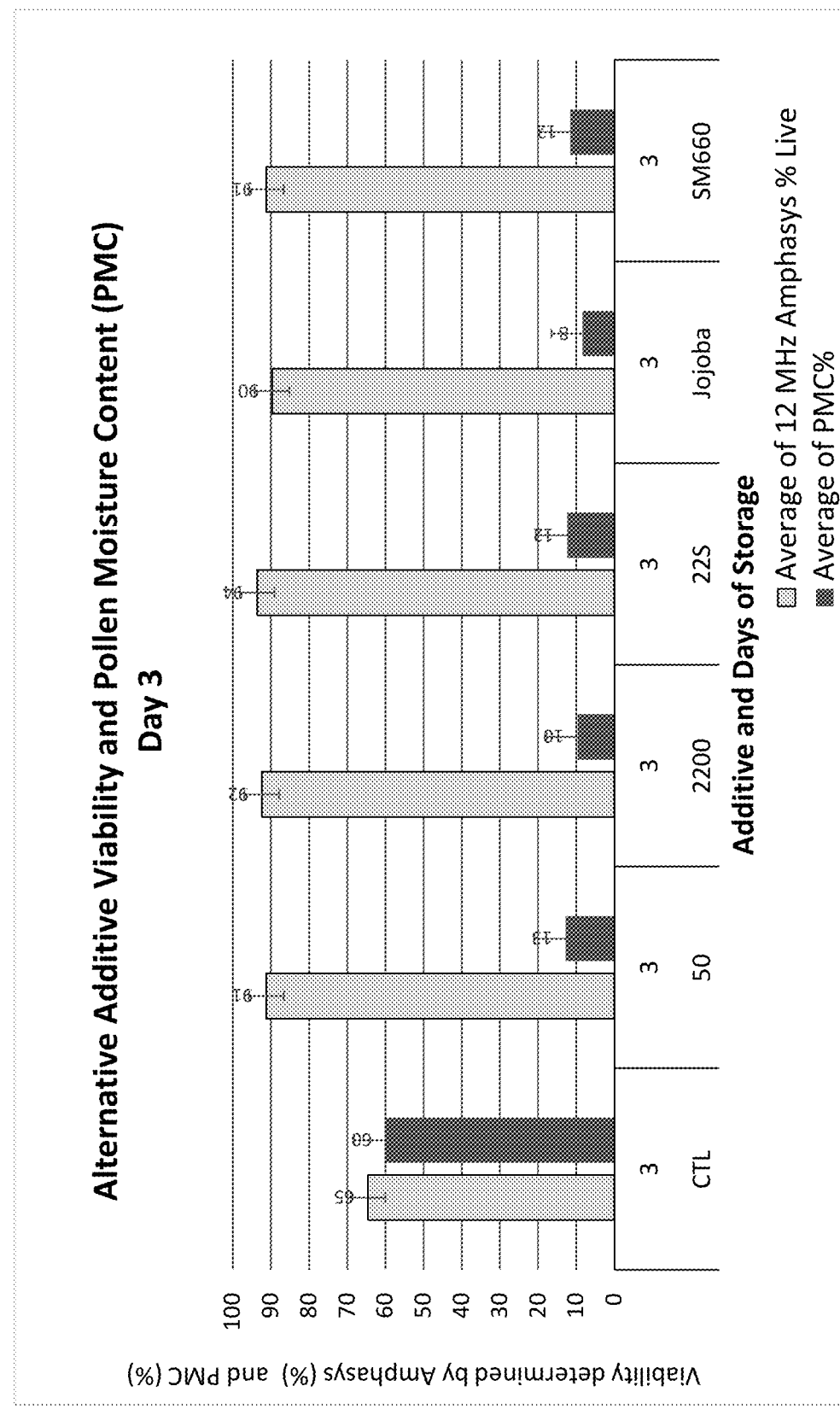
FIG. 7 shows the data collected from working example 7. The experiment used mixed maize pollen collected from a growth chamber. The pollen was stored with a variety of different media all comprising 98% lactose, and 2% of a series of different substances intended to improve flowability. The figure shows the viability and PMC of the pollen after 3 days of storage.
Figure 8:
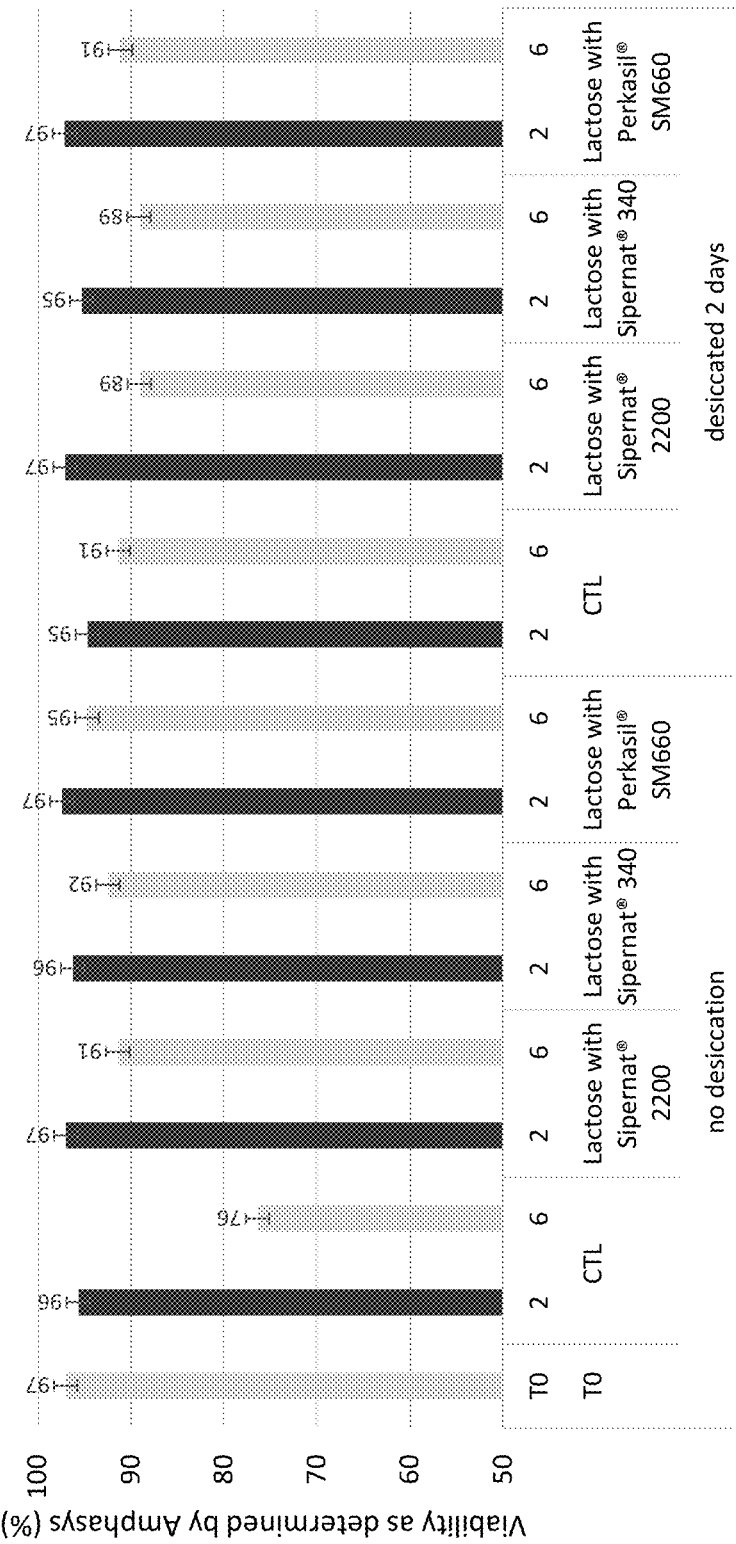
FIG. 8 shows the data collected from working example 8. The experiment used mixed maize pollen collected from a growth chamber. The pollen was stored with a variety of different media all comprising 98% lactose, and 2% of a series of different substances intended to improve flowability. Some samples were subjected to a 2-day desiccation period and others were not. The figure shows the viability and PMC of the pollen after 2 and 6 days of storage.

In order to study the effect of storage compound particle size on pollen separation and storage, a series of solid particulate compositions were used for pollen storage and application to silks on growing maize plants. Fresh pollen was harvested from actively shedding maize plants. The pollen was divided into six equal samples, which were placed into individual 50 mL centrifuge tubes. Each sample subsequently had an equal ratio of silica particles of a specific size added to the pollen. The sizes of the added silica particles ranged from 5.5μ up to 340μ. After the addition of the particles, each tube was mixed and placed into storage at 4° C. for 24 hours. Hand pollinations from the mixture in each tube were then conducted with 5 shoot-bagged ears and the ears were bagged post pollination to prevent additional pollen from landing on the silks. The ears were allowed to mature, after which they were harvested and the total number of kernels per ear was counted. The data is presented in FIG. 6. The 20μ particle size produced the highest average kernel number but the remainder of the particle sizes also produced kernels with varying rates of efficacy. This experiment demonstrates how the optimal particle size can be identified for a specific pollen size

EXAMPLE 7

In order to further study the effect of particle size on pollen separation, storage and flowability, a series of solid particulate compositions were used for long term storage of pollen. Different additives were used in a lactose base separation compound to test for improved flowability of pollen for eventual use in mechanical application of the pollen in a field setting.

TABLE 1

| Particulate Substance | Additive | Additive particle size (microns) |
|---|---|---|
| 98% Lactose | 2% Sipernat ® 2200 | 320 |
| 98% Lactose | 2% Jojoba beads | 150-250 |
| 98% Lactose | 2% Sipernat ®50 | 50 |
| 98% Lactose | 2% Sipernat ®22S | 14 |
| 98% Lactose | 2% Perkasil ® SM660 | 16 |

Maize tassels, of pooled varieties and in the beginning stage of active anthesis, were harvested and stored in a Conviron® growth chamber. To prolong the productivity of the tassels, the Conviron® growth chamber was programmed to run at 12° C. and 90% RH for 18 hours, 26° C. and 70% RH for 6 hours, for collection purposes. Pooled pollen was hand collected from maize tassels and mixed at a 1:3 volume ratio with each additive from Table 1. A control sample was also prepared containing just pollen without any storage medium. The control samples and sample mixtures of pollen and particulate were stored in filter capped 50 mL centrifuge tubes which are retained in an enclosed larger sealed container that had approximately 100 mL of Dry-Dry silica bead desiccant. The filter caps have a mesh element that allows passage of air without spilling the pollen. The sealed container was stored in a growth chamber at 3° C. This maintains a microclimate that is cold and slightly dry for the storage of the filter capped tubes.

It was noted at the time of mixing the samples that the jojoba beads and Sipernat® 2200 mixtures were difficult to work with because they caused clumping of the mixture, implying poor flowability.

T0 viability using Amphasys was 89.26% at the beginning of the test period. After three days of storage, the stored pollen samples were tested using the Amphasys system to measure viability. Amphasys provides a reliable determination of pollen viability using an impedance flow cytometer, which measures the electrical properties of pollen grains.

As shown in FIG. 7, the control sample showed a small reduction in viability and had poor flowability due to high PMC. All other tested samples showed strong viability and flowability.

EXAMPLE 8

A series of solid particulate compositions were used for long term storage of pollen with and without desiccant treatment. Different additives were used to test for improved flowability of pollen for use in mechanical application of the pollen in a field setting.

TABLE 2

| Particulate Substance | Additive | Additive particle size (microns) |
|---|---|---|
| 98% Lactose | 2% Sipernat ® 340 | 20 |
| 98% Lactose | 2% Sipernat ® 2200 | 320 |
| 98% Lactose | 2% Perkasil ® SM660 | 16 |

Maize tassels, of pooled variety and in the beginning stage of active anthesis, were harvested and stored in a Conviron® growth chamber. To prolong the productivity of the tassels, the Conviron® growth chamber was programmed to run at 12° C. and 90% RH for 18 hours, 26° C. and 70% RH for 6 hours, for collection purposes. Pooled pollen was hand collected from maize tassels and mixed at a 1:3 volume ratio (1 mL of pollen was added to 3 mL of the composition) with the compositions from Table 2. Control samples were also created with solely pollen and no particulate medium composition. The samples were stored in filter-capped sample tubes. The filter caps have a mesh element that allows passage of air but prevents spilling the tube contents. Two identical sets of samples were prepared. One set of samples was mixed and stored in a closed container containing desiccant as outlined in Example 7 for two days of storage. The second set of samples were also stored in a container but without any desiccant. After two days of storage, all samples from the container with desiccant were moved to a container without desiccant. The purpose of this experiment was to demonstrate any enhancement of viability by lowering the pollen moisture content slightly, but not excessively.

T0 viability using Amphasys was 97% at the beginning of the test period. After two and six days of storage, the stored pollen was tested using the Amphasys system to measure viability. Amphasys provides a reliable determination of pollen viability using an impedance flow cytometer, which measures the electrical properties of pollen grains. The data is presented in FIG. 8.

With the exception of the control sample, all the non-desiccated samples performed better than the samples exposed to desiccant. This was the case at Day 2 and Day 6. All samples showed strong viability at 6 days. In this case, desiccation with additives did not increase viability during storage. All samples that were mixed with the compositions had better viability than the control sample.

EXAMPLE 9

Pollen storage with and without desiccant was tested to determine the effect of the desiccant on the pollen viability. Maize tassels of mixed varieties and ages were harvested and stored in a Conviron® growth chamber. To prolong the productivity of the tassels, the Conviron® growth chamber was programmed to run at 12° C. and 90% RH for 18 hours, 26° C. and 70% RH for 6 hours, for collection purposes. Pollen totaling just over 3 grams was collected from the growth chamber tassels by tapping the tassels over a screen that allowed pollen to pass through without allowing the anthers to pass. Pouches were formed from Whatman filter paper #4, and 1.75 g of fresh pollen was added to each pouch. The pouches were rolled and placed into 50 mL conical tubes. Some tubes contained 30 mL of Dry & Dry silica gel bead desiccant. The tubes were capped and stored at 3° C. for three days.

Testing conducted at 3 days using Amphasys demonstrated that the pollen stored with the desiccant had a pollen moisture content (PMC) of 10.9% and viability of 0.67%. The pollen stored without the desiccant had a PMC of 57% and viability of 91.52%.

This experiment demonstrated that too much contact with desiccant does not support pollen viability and longevity during cold storage.

EXAMPLE 10

A study was conducted to determine if there was an effect on pollen viability based on the ratio of pollen to physical pollen separation compound. Maize tassels harvested and shipped from Hawaii, of pooled variety and in the beginning stage of active anthesis, were stored in a Conviron® growth chamber. To prolong the productivity of the tassels, the Conviron® growth chamber was programmed to run at 12° C. and 90% RH for 18 hours, 26° C. and 70% RH for 6 hours, for collection purposes. Pooled pollen was hand collected from the maize tassels and a small portion of the time zero pollen was tested for viability using Amphasys, which resulted in 96 percent viability.

Figure 9:
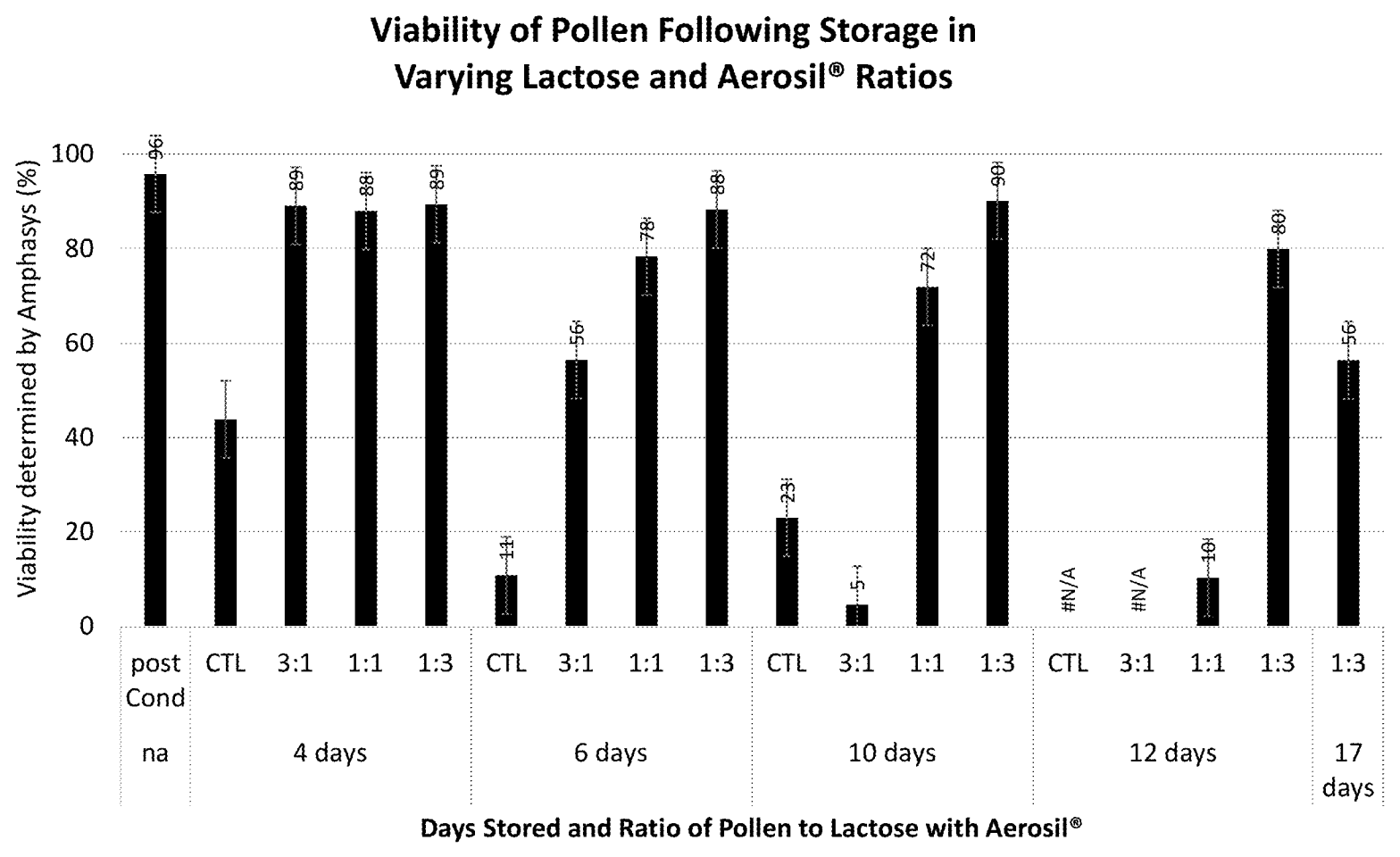

The remainder of the pollen was divided into four equal amounts and placed in 50 mL centrifuge tubes. and mixed at three different weight ratios with a separation compound comprising 96% lactose and 4% Aerosil®. The first tube served as a control and no separation compound was added to it. The second tube had a ratio of 3:1, pollen to separation compound. The third tube had a ratio of 1:1, pollen to separation compound. The fourth tube had a ratio of 1:3, pollen to separation compound. Each tube was thoroughly inverted to mix the pollen in with the separation compound and placed into storage at 4° C. Each tube was checked for pollen viability after 4, 6, 10, 12 and 17 days using Amphasys. The data is presented in FIG. 9.

After 4 days in storage, all ratios of pollen with separation compound were outperforming the control. After 6 days in storage, the 3:1 ratio of pollen to separation compound began to sharply decline in viability when compared to the 1:1 and 1:3 ratios, however it still out-performed the control. The 1:1 ratio of pollen to separation compound also began to decline in viability. After 10 days in storage, the same trends continued. After 12 days, both the control sample and the 3:1 ratio sample showed no viable pollen. The 1:1 sample showed low levels of viability, however the 1:3 ratio sample still demonstrated 80 percent viability. Even after 17 days, the 1:3 ratio sample tested at 56 percent viability. This test provided further confirmation that the more separation occurring between grains of pollen during storage to minimize contact, the longer the pollen will remain viable during the period of storage.

EXAMPLE 11

In order to determine whether the method of maintaining pollen separation was effective in other plant species, experiments were conducted with wheat. Wheat heads of Grandin wheat variety were collected at early emergence stage and post-emergence stage. At the post emergence stage, a few anthers were exposed on the wheat heads. The anthers were collected from a subsample of the heads and the collected anthers were ground with a nylon pestle in 1.5 mL of Ampha 6 media, filtered, and run through the Amphasys system to measure T0 viability. Amphasys provides a reliable determination of pollen viability using an impedance flow cytometer, which measures the electrical properties of pollen grains.

A second subsample of the early emergence stage and post-emergence wheat heads were taken from different regions of each head. These samples were stored whole at 5° C. in cryo vials. The samples in the vials had either no storage medium, lactose particulate storage medium, or lactose (Lab grade D-lactose monohydrate, RPI #L26100-1000.0) combined with 2% Sipernat® 340 storage medium. After storage for either 3 or 14 days, pollen was extracted from the stored anthers using the nylon pestle, and viability was determined using Amphasys.

The pollen viability from the samples is provided in Table 3, below.

TABLE 3

Wheat Pollen Viability

| Storage Medium | Early Emergence Heads Viability (%) | Post-emergence Heads Viability (%) |
| --- | --- | --- |
| T0 | 22-42% | 19-42% |
| Day 3, no medium | 40-49% | 26-35% |
| Day 3, lactose only | 28-41% | 27-35% |
| Day 3, lactose plus Sipernat ® 340 | 32-41% | 22-36% |
| Day 14, no medium | 13-25% | 21-43% |
| Day 14, lactose only | 39-44% | 6-17% |
| Day 14, lactose plus Sipernat ® 340 | 17-23% | 13-16% |

Figure 10:
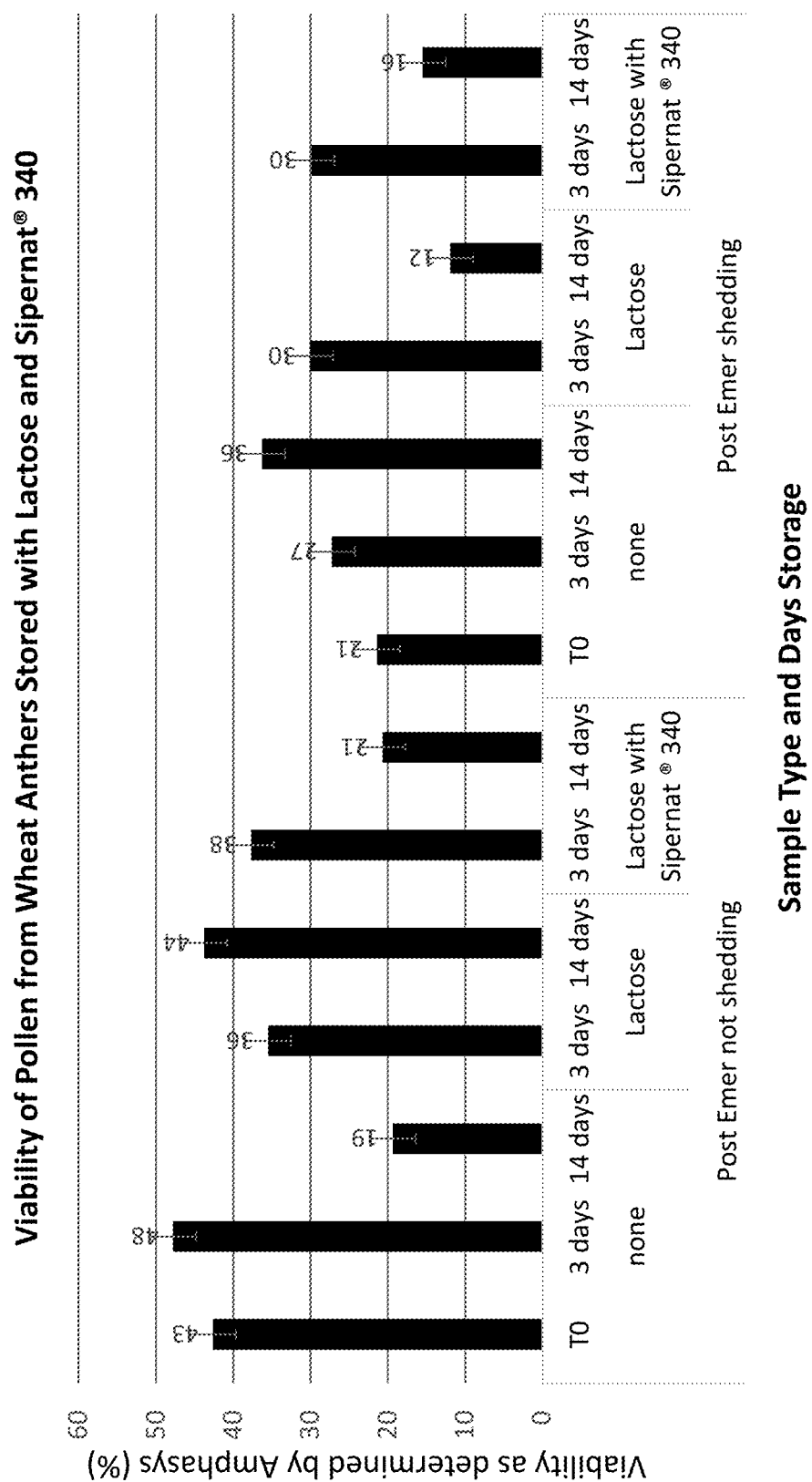
FIG. 10 shows the data collected from working example 11. The experiment used pollen from stored wheat anthers collected both post-emergence but not shedding pollen, and post-emergence and shedding pollen. The anthers were stored with no medium as a control, with powdered lactose, or with a combination of lactose and Sipernat® 340. The figure shows the viability of the pollen after 3 and 14 days of storage.

The results of this experiment are presented in FIG. 10. At 3 days, there was a small improvement in viability when compared to T0 data in the early-emergence anthers. The mature anthers produced similar viability regardless of treatment. The storage in the lactose-based media shows an advantage.

EXAMPLE 12

Another experiment was conducted to test the efficacy of maintaining separation of pollen grains in rice. Rice anthers were collected from a pool of cut back glumes. One sample of the anthers was ground with a nylon pestle in 1.5 mL of Ampha 6 media, filtered, and run through the Amphasys system to measure T0 viability. Amphasys provides a reliable determination of pollen viability using an impedance flow cytometer, which measures the electrical properties of pollen grains.

Figure 11:
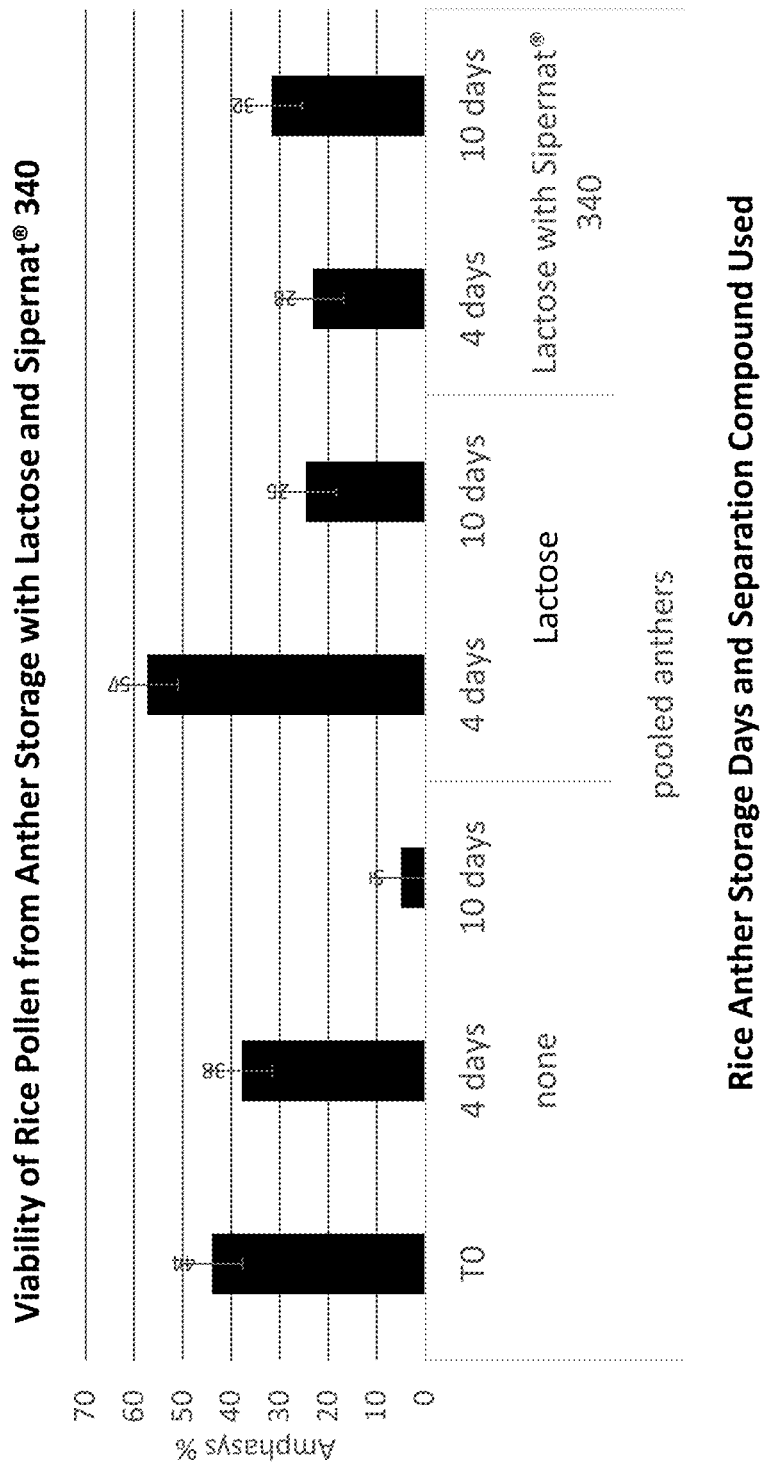
FIG. 11 shows the data collected from working example 12. The experiment used pollen from stored, pooled rice anthers. The anthers were stored with no medium as a control, with powdered lactose, or with a combination of lactose and Sipernat® 340. The figure shows the viability of the pollen from the anthers after 4 and 10 days of storage.

A second subsample of the anthers was divided into three groups that were stored whole at 5° C. in cryo vials. These samples were stored whole at 5° C. in cryo vials. The samples in the vials had either no storage medium, lactose particulate storage medium, or chemical grade lactose combined with 2% Sipernat® 340 storage medium. After storage for either 4 days or 10 days, pollen was extracted from the stored anthers using the nylon pestle, and viability was determined using Amphasys. The data is shown in FIG. 11.

The pollen viability from the samples is provided in Table 4, below.

TABLE 4

Rice Pollen Viability

| Storage Medium | Pollen Viability (%) |
| --- | --- |
| T0 | 44-55% |
| Day 4, no medium | 36-38% |
| Day 4, lactose only | 57-63% |
| Day 4, lactose plus Sipernat ® 340 | 23-35% |

TABLE 4-continued

Rice Pollen Viability

| Storage Medium | Pollen Viability (%) |
| --- | --- |
| Day 10, no medium | 0-5% |
| Day 10, lactose only | 24-27% |
| Day 10, lactose plus Sipernat ® 340 | 27-34% |

At 4 days, there was an improvement in viability of pollen when compared to T0 data of pollen from the anthers stored in the lactose-only media.

EXAMPLE 13

Figure 12:
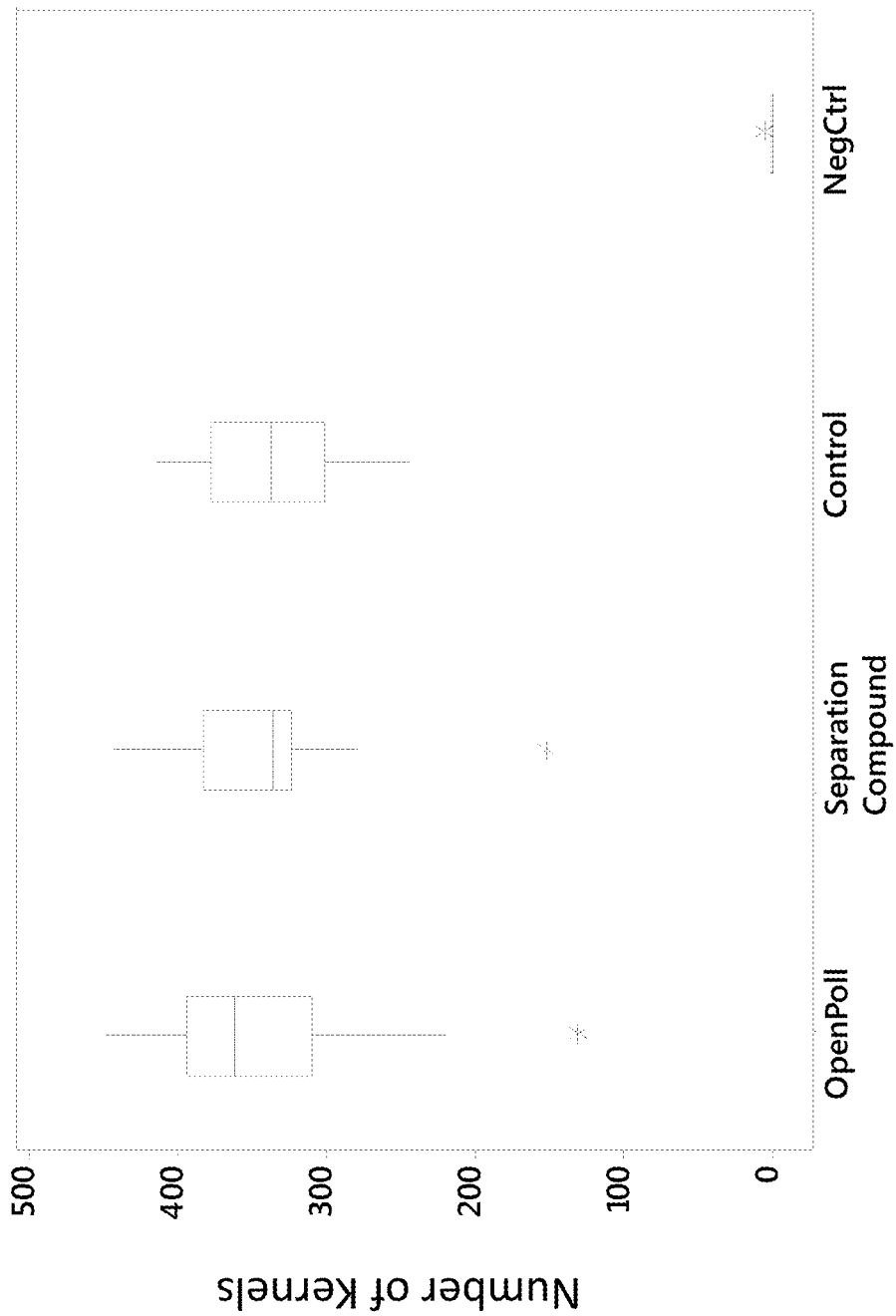
FIG. 12 shows the data collected from working example 13. A kernel set experiment was conducted using pollen that had been stored with a separation compound in order to compare the kernel set from open pollination and a fresh pollen control. The figure shows the number of kernels resulting from each sample.

A kernel set experiment was conducted to determine if the pollen stored with a separation compound would result in more or fewer kernels than fresh pollen application or open pollination. For this experiment, test plants of a single genotype were shoot bagged in the field with the exception of a group of open pollinated plants, which were allowed to naturally pollinate. The negative control plants never had the shoot bags removed. For the control pollinations, a bulk of freshly shedding pollen was collected and divided into two portions. The first portion was used to hand pollinate the control plants, at which time they were bagged to prevent additional pollen from accumulating on the silks. The second bulk of pollen was mixed with a 1:1 ratio of fresh pollen to a separation compound of 98 percent lactose and 2% Sipernat 340. These pollen samples were stored at 4° C. for 24 hours. After 24 hours the shoot bags were removed from the plants reserved for the separation compound tests, the pollen mixed in the separation compound was applied to the silks, and the plants were again shoot bagged to prevent additional pollen from accumulating on the silks. All pollinated plants were allowed to mature and ears from each treatment were harvested. Kernel counts were conducted on each ear and the data is presented in FIG. 12. The data shows that there was no statistical difference between the open pollinated plants, the control plants or the plants pollinated with the pollen stored with the separation compound. This demonstrates that the pollen stored with the separation compound retains full viability and resulted in a higher kernel number than the control ears pollinated with fresh pollen.

EXAMPLE 14

This example tested the performance of 97% lactose mixed with 3% Sipernat® D17 as a separation compound. Freshly shedding pollen was harvested from maize tassels and the T0 viability was measured at 95.8 percent using Amphasys. The remainder of the pollen was mixed in a 1:1 volume ratio with the separation compound. The viability of the pollen was measured using Amphasys at 3 and 7 days and hand pollinations were conducted on shoot bagged ears at each interval with a bag placed over the silks post pollination to prevent additional pollen from landing on the silks. Although each storage interval contained viable pollen, the field pollinations failed to produce kernels. Upon closer examination of the additive mixture with the pollen it became evident that the Sipernat® D17 product, which is slightly hydrophobic, was coating the pollen, preventing it from binding to the silks when applied.

Figure 13:
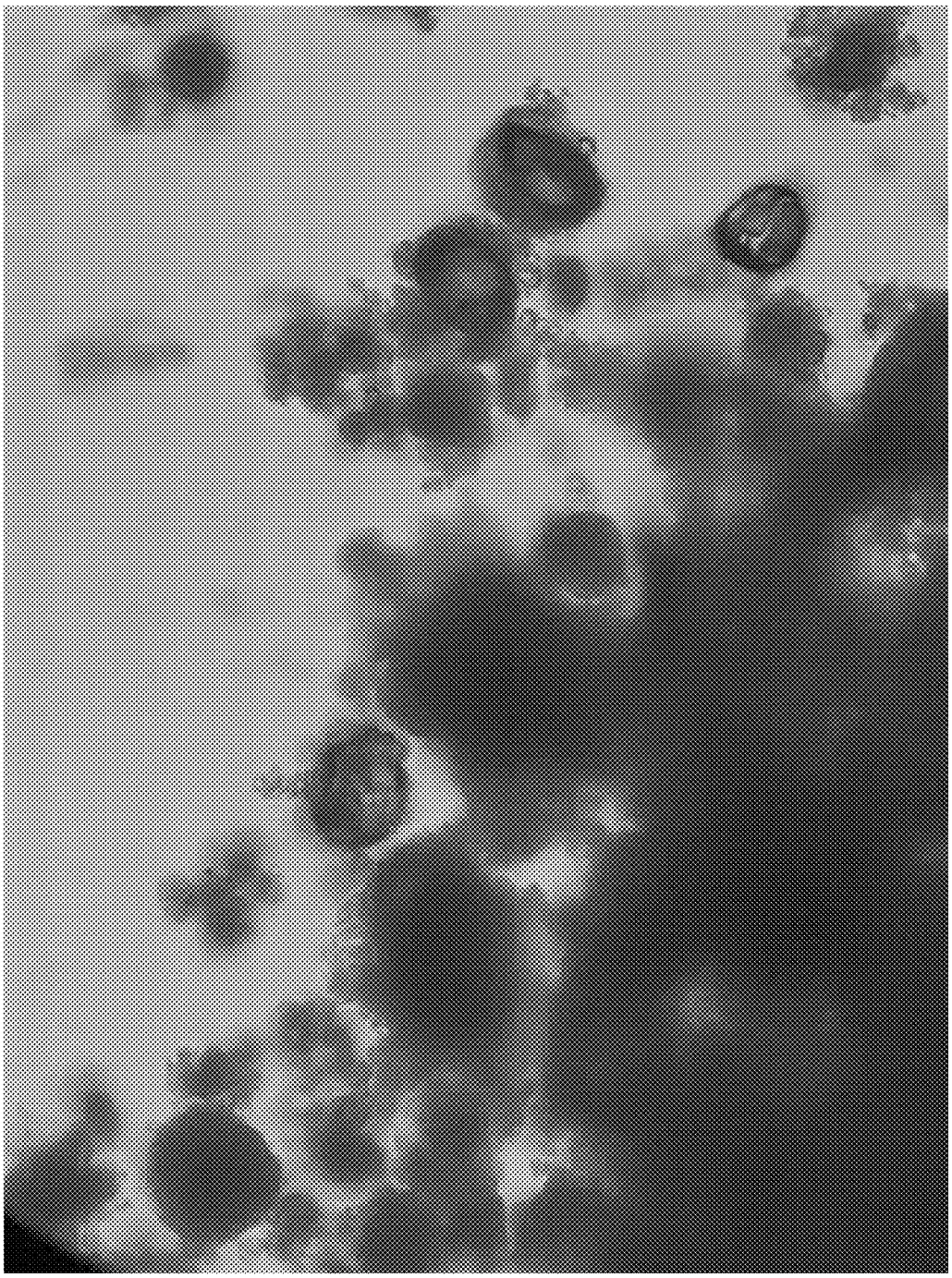
FIG. 13 shows pollen that had been combined with Sipernat® D17. The figure demonstrates the coating of the particles on the pollen, which resulted in a slippery surface, thereby preventing the pollinations from being successful.

FIG. 13 provides a microscopic image of the pollen coated with the Sipernat® D17 product. The coating on the pollen resulted in a slippery surface, preventing the pollinations from being successful in spite of the fact that the pollen was viable. In addition, the image shows that the pollen grains are still reasonably well hydrated after 14 days of storage. This experiment demonstrates that routine experimentation can easily test various separation compounds for efficacy and can easily identify those compounds which are most suitable for the pollen and plant structures of interest.

EXAMPLE 15

Figure 14:
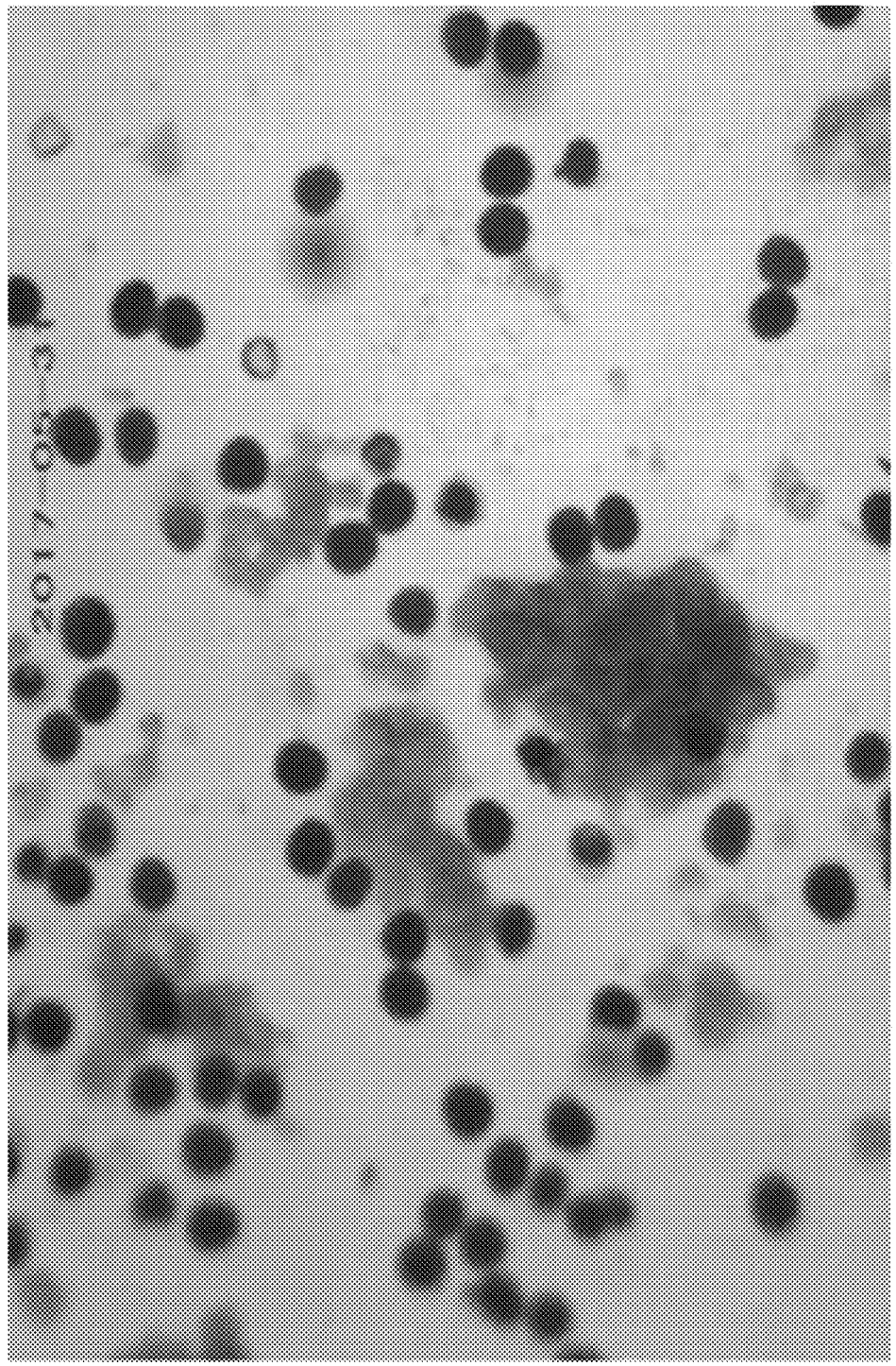
FIG. 14 shows pollen that had been combined with casein as provided in working example 15. The figure demonstrates that casein has a negative impact on pollen viability, resulting in little to no viability when stored for 20 hours at 4 degrees Celsius.
Figure 15:
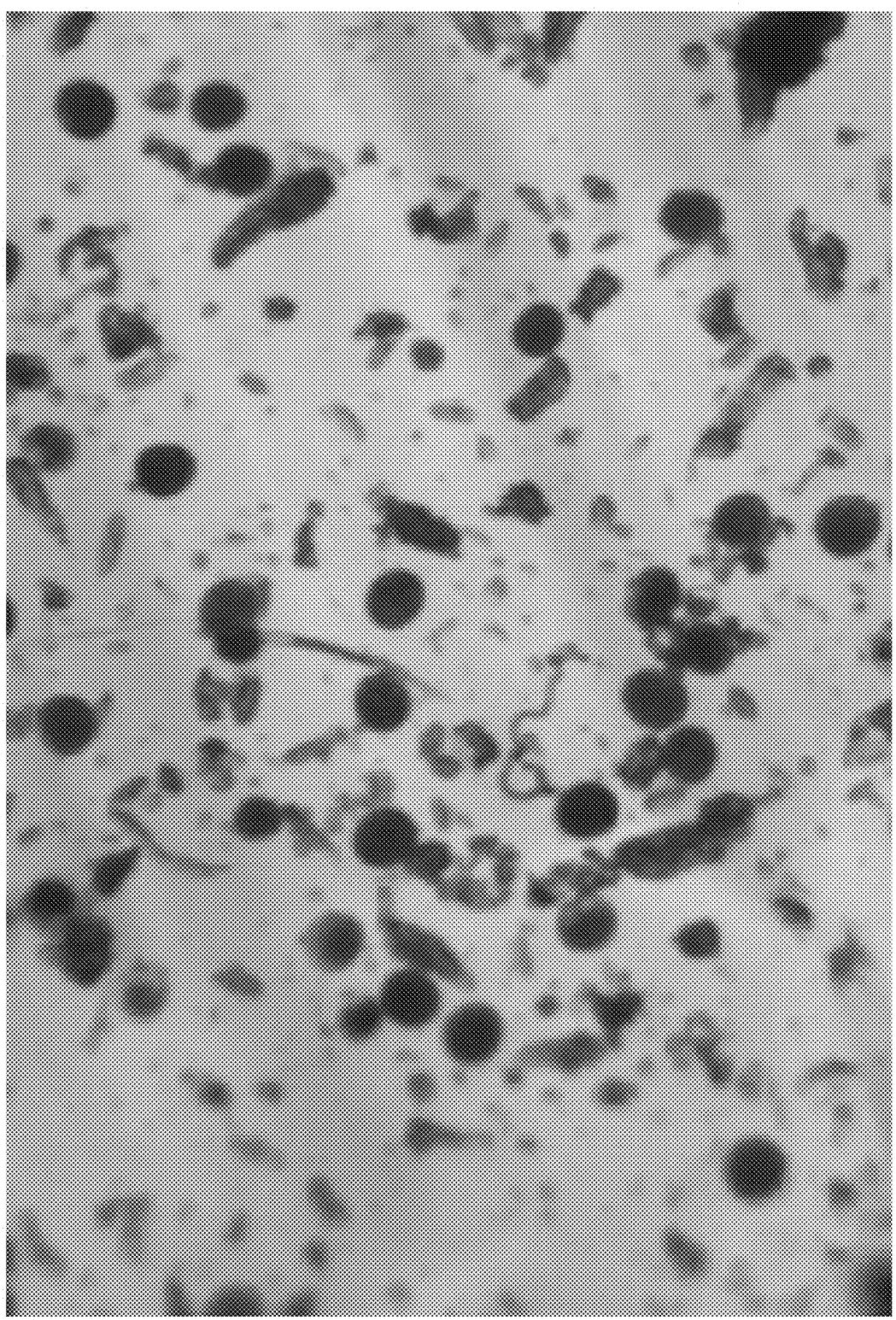
FIG. 15 shows pollen that had been combined with cellulose as provided in working example 15. The figure demonstrates that cellulose has a negative impact on pollen viability, resulting in decreased viability when stored for 20 hours at 4 degrees Celsius.

Casein and cellulose were both tested separately as possible substances for maintaining or increasing pollen viability. Previous literature has suggested that casein in particular is a substance that is compatible with pollen. Freshly harvested maize pollen was harvested from actively shedding tassels. The pollen was divided into two equal portions, each of which was placed into a 50 ml centrifuge tube. The first tube had an equal portion of casein added to the tube. The second tube had an equal portion of cellulose added to the tube. Each tube was stored for 24 hours at 4 degrees Celsius. A germination assay was conducted after 24 hours. The results show that both casein and cellulose are detrimental to the viability of pollen, as shown in FIGS. 14 and 15. Namely, FIG. 14 shows that pollen mixed with casein is largely, if not completely unviable after 20 hours of storage at 4 degrees Celsius. Moreover, FIG. 15 shows that pollen mixed with cellulose has little viability after 20 hours of storage at 4 degrees Celsius.

EXAMPLE 16

Figure 16:
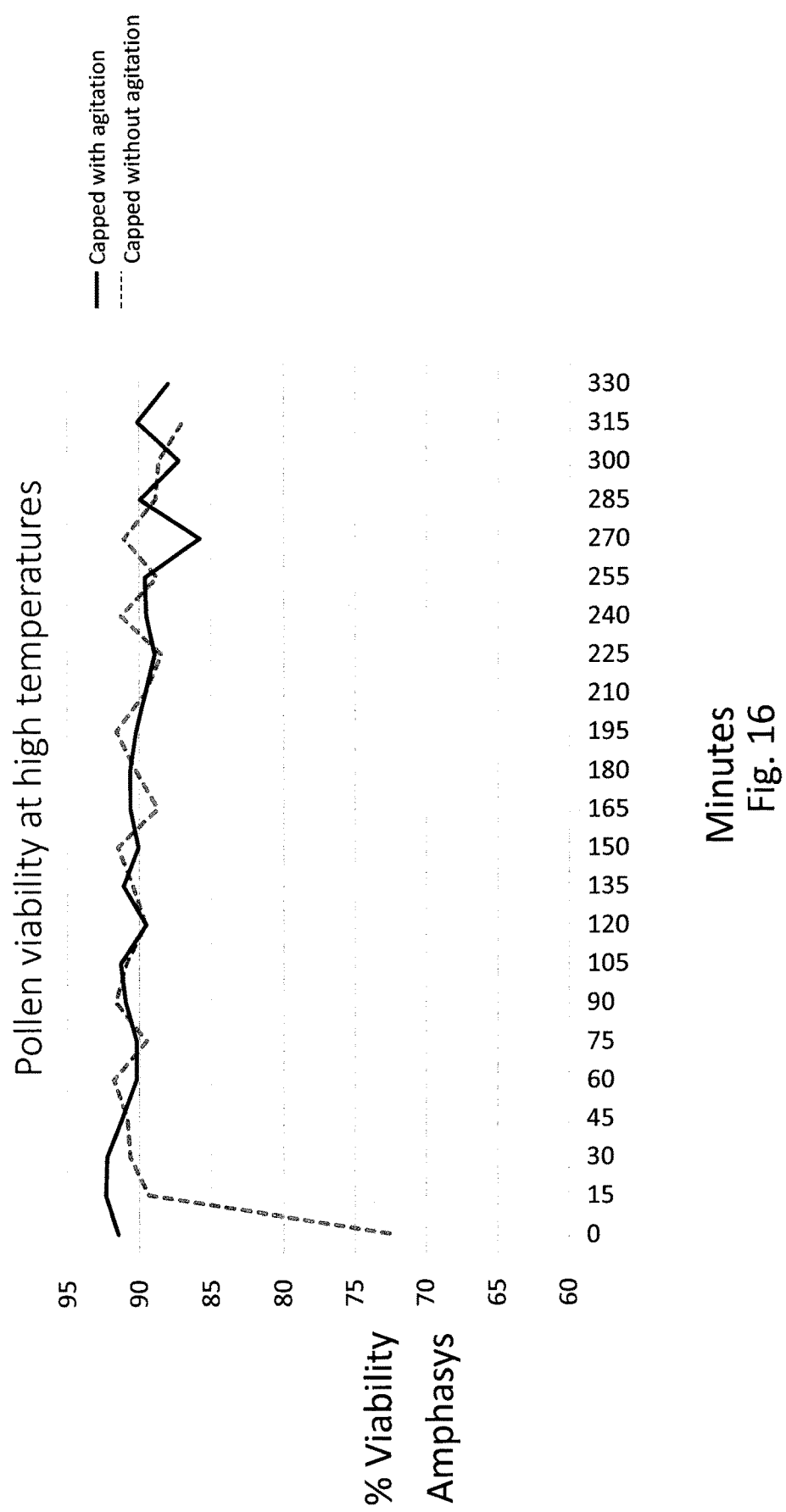
FIG. 16 shows the data collected in working example 16. Namely, the figure shows good viability when storing pollen according to methods of the present invention. Maize pollen was stored with a mix of lactose and Sipernat 340 at 29.6 and 32.8 degrees Celsius resulting in good viability.

Tests were conducted to determine the performance of the invention under hot conditions. In the experiment, a bulk of fresh pollen was harvested. A time zero pollen viability was conducted using Amphasys. The pollen was then mixed with a 1:5 ratio of 1 part pollen, 5 parts 98% lactose and 2% Sipernat 340. The mix was allocated into 2 different one quart containers, each containing a total volume of 100 mL's. The first container was capped and swirled prior to taking a sample for viability testing ensuring that there was no bias based on the layers of pollen in the container. The second container was capped and not swirled prior to taking a sample for viability testing on Amphasys. Both containers were placed into direct sun during testing. Temperature ranged from 29.6 degrees Celsius to 32.8 degrees Celsius throughout the testing period. The data showed that the pollen in each treatment remained highly viable throughout 330 minutes of exposure to the heat, as shown in FIG. 16.

EXAMPLE 17

Figure 17:
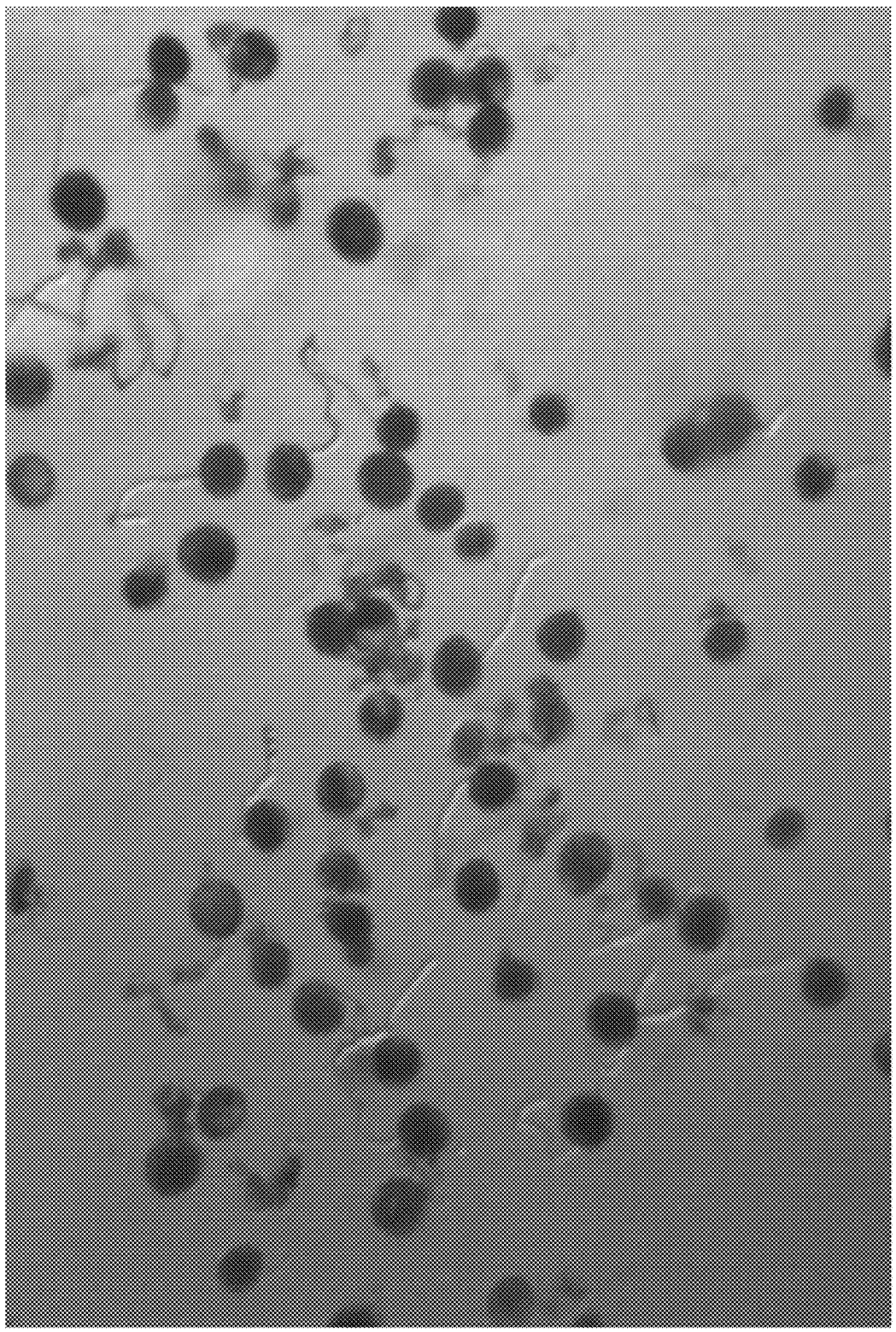
FIG. 17 shows the results of working example 17. Namely, the figure shows that storage of maize pollen in Sonneborn® PD-23 mineral oil resulted in good pollen viability.

Sonneborn® PD-23 mineral oil was tested as a pollen separation agent. This substance was a liquid at all stages of the described experiment. Freshly harvested pollen from a bulk of maize plants was placed into mineral oil and stored at 4 degree Celsius for a period of 20 hours. After 20 hours, germination media was applied into the oil formulation. The results supported that liquid serves as a proficient storage media for pollen. Furthermore, pollen grains which were in direct contact with one another mostly failed to germinate, while a high percentage of pollen grains not in contact with other pollen grains formed a pollen tube. This further supports the concept that separation of pollen grains increases viability. Results are shown in FIG. 17.

The invention claimed is:

1. A method of preserving the integrity and viability of live pollen grains comprising:
   a. preserving pollen, including both live pollen grains and dead pollen contents that have leaked from dead or dying pollen cells, by introducing said live pollen grains and dead pollen contents to at least one solid particulate substance wherein said solid particulate substance prevents said dead pollen contents from interacting with said live pollen grains during the period of preservation; and
   b. following said period of preservation and within a period of time that will result in seed set, applying said pollen including both dead pollen contents and live pollen grains to a plant such that at least one of said live pollen grains successfully pollinates said plant.

2. The method of claim 1 comprising storing said pollen with at least one solid particulate substance.

3. The method of claim 1 wherein said at least one solid particulate substance surrounds or isolates at least one pollen grain.

4. The method of claim 1 wherein said at least one solid particulate substance minimizes surface-to-surface contact between a plurality of pollen grains.

5. The method of claim 1 wherein pollen moisture content is maintained at 15-60%.

6. The method of claim 5 wherein said pollen moisture content is maintained at 35-60%.

7. The method of claim 1 wherein the ratio of said at least one solid particulate substance to said pollen grains is at least 1:1.

8. The method of claim 7 wherein the ratio of said at least one solid particulate substance to said pollen grains is at least 3:1.

9. The method of claim 1 wherein the size of said at least one solid particulate substance ranges from a maximum of ten times larger than the size of said pollen grains to a minimum of ten times smaller than the size of said pollen grains.

10. The method of claim 9 wherein said solid particulate substance includes particles of varying sizes.

11. The method of claim 1 wherein said solid particulate substance is selected from the group consisting of lactose, Sipernat® 50, Sipernat® 50S, Sipernat® 2200, Sipernat® 22, Sipernat® 22S, Sipernat® 340, Sipernat® 350, Perkasil® SM660, Jojoba beads, Aerosil® 200, Syloid® 244, and combinations thereof.

12. The method of claim 1 wherein said pollen is selected from the group consisting of freshly collected pollen and stored pollen.

13. The method of claim 1 further comprising field conditioning said pollen.

14. The method of claim 1 wherein said solid particulate substance is selected from the group consisting of solid inorganic particles and solid organic particles.

15. The method of claim 14 wherein said solid particulate substance is selected from the group consisting of sand, dry sugars, and activated charcoal.

16. The method of claim 1 wherein said method includes mixing said pollen and said at least one solid particulate substance.

17. The method of claim 16 wherein said mixing is continuous.

* * * * *